(12) United States Patent
Potthoff et al.

(10) Patent No.: US 7,479,378 B2
(45) Date of Patent: Jan. 20, 2009

(54) METHOD OF ANALYZING ENZYME COMPOSITIONS WITH LIPOLYTIC, PROTEOLYTIC AND AMYLOLYTIC ACTIVITY

(75) Inventors: Andreas Potthoff, Hannover (DE); Andreas Koerner, Springe (DE); Bernd Thumbeck, Nordstemmen (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 58 days.

(21) Appl. No.: 10/901,436

(22) Filed: Jul. 29, 2004

(65) Prior Publication Data

US 2005/0112743 A1 May 26, 2005

Related U.S. Application Data

(60) Provisional application No. 60/490,510, filed on Jul. 29, 2003.

(51) Int. Cl.
*C12Q 1/37* (2006.01)
(52) U.S. Cl. ........................................................ 435/23
(58) Field of Classification Search .................. None
See application file for complete search history.

(56) References Cited

U.S. PATENT DOCUMENTS

| 4,019,958 | A | | 4/1977 | Hell et al. | |
|---|---|---|---|---|---|
| 4,623,624 | A | * | 11/1986 | Schultze | 435/186 |
| 6,278,794 | B1 | * | 8/2001 | Parekh et al. | 382/129 |

FOREIGN PATENT DOCUMENTS

WO        99/28344        6/1999

OTHER PUBLICATIONS

Bieger et al, "Two-dimensional Isoelectric Focusing/Sodium Dodecyl Sulfate Gel Electrophoresis of Protein Mixtures Containing Active or Potentially Active Proteases: Analysis of Human Exocrine Pancreatic Proteins," (Analytical Biochemistry), vol. 109, 1980, pp. 222-230.*
Padfield et al, The Use of Two-Dimensional Gel Electrophoresis and High-performance Liquid Chromatography for the Analysis of Pancreatic Juice, (The Pancreas: Biology, Pathobiology, and Disease), Second Edition, Chapter 14, pp. 265-273.*
"Pancreatin." The American Heritage Dictionary of the English Language, 4th Edition Boston: Houghton Mifflin, 2000. www.bartleby.com/61/. (printed Mar. 21, 2007).*
"Pancreatic juice." The American Heritage Dicitonary of the English Language, 4th Edition Boston: Houghton Mifflin, 2000. www.bartleby.com/61/. (printed Mar. 21, 2007).*
Article entitled, "ICH Harmonised Tripartite Guideline", table of contents and pp. 1-16.
Article entitled, "Liquid Chromatography" pp. 1-3.
Article entitled, "Electrophoresis", pp. 1-9 dated Dec. 28, 2004.

Article by Scharpe, S. et al entitled, "Isoelectric Characterization of Porcine Pancreative Alpha.Amylases", Journal De Pharmacie De Belgique, vol. 28, No. 6, 1973, pp. 705-708.
Article by Shimura K. et al entitled, "Affinophoresis in Two-Dimensional Agarose Gel Electrophoresis Specific Separation of Biomolecules by a Moving Affinity Ligand", Analytical Biochemistry, vol. 161, No. 1, 1987, pp. 200-206.
Dony et al., "Etude électrophorétique et immunoélectrophorétique de préparations enzymatiques injectables: préparations d'origine pancréatique et préparations d'origine testiculaire", *Progress In Immunological Standardization*, vol. 4, pp. 395-405 (1970).
English Abstract of Dony et al., "Electrophoretic and immunoelectrophoretic study of injectable enzymic preparations: preparations of pancreatic origin and preparations of testicular origin", *Progress In Immunological Standardization*, vol. 4, pp. 395-405 (1970).
Padfield et al., "The Use of Two-Dimensional Gel Electrophoresis and High-Performance Liquid Chromatography for the Analysis of Pancreatic Juice", T*he Pancreas: Biology, Pathobiology, and Disease*, Second Edition, Chapter 14, pp. 265-273 (1993).
International Search Report mailed on Nov. 24, 2004 in International Application No. PCT/EP2004/008332, European Patent Office.
International Preliminary Report On Patentability issued on Jan. 30, 2006 in International Application No. PCT/EP2004/008332, International Bureau of WIPO.
Challapalli et al., High reproducibility of large-get two-dimensional electrophoresis, Electrophoresis, vol. 25 (2004) p. 3040-3047.
Van Den Bergh et al., Fluorescent two-dimensional difference gel electrophoresis and mass spectrometry identify age-related protein expression differences for the primary visual cortex of kitten and adult cat, Journal of Neurochemistry, vol. 85 (2003) p. 193-205.
Voss et al., Observations on the reproducibility and matching efficiency of two-dimensional electrophoresis gels: Consequences for comprehensive data analysis, Electrophoresis, vol. 21 (2000) p. 3345-3350.
Hagler et al., Maximising reproducibility and improving the resolution of target proteins with automated gradient gel casting for 2D electrophoresis (2005).
Nishihara, et al., "Quantitative evaluation of proteins in one- and two-dimensional polyacrylamide gels using a fluorescent stain", Electrophoresis 2002, 23, 2203-15 (2002).
Smolka, et al., "Quantitative protein profiling using two-dimensional gel electrophoresis, isotope-coded affinity tag labeling, and mass spectrometry", Molecular & Cellular Proteomics 1.1, 19-29 (2002).
Goerg, et al., "The current state of two-dimensional electrophoresis with immobilized pH gradients", Electrophoresis 2000, 21, 1037-53 (2000).

(Continued)

*Primary Examiner*—Ralph Gitomer
*Assistant Examiner*—Amanda P Wood
(74) *Attorney, Agent, or Firm*—Mayer Brown LLP

(57) ABSTRACT

A method for analyzing the identity, protein and/or peptide pattern and also the stability of samples containing physiologically acceptable enzyme mixtures with lipolytic, proteolytic and amylolytic activity, particularly mixtures of digestive enzymes such as pancreatin, for use in manufacturing medicinal products comprising such enzyme mixtures, e.g. precipitated pancreatin or pancreatin mini-microspheres.

22 Claims, 8 Drawing Sheets

OTHER PUBLICATIONS

Scheele, "Two-dimensional gel analysis of soluble proteins", J. Biol. Chem., vol. 250, No. 14, Issue Jul. 25, 5375-85 (1975).

Ridder et al., "Quantitative Analysis of pattern recognition of two-dimensional electrophoresis gels", Clin. Chem. 30/12, 1919-24 (1984).

Goldman et al., "Human lymphocyte polymorphisms detected by quantitative two-dimensional electrophoresis", Am. J. Hum. Genet. 35:827-837 (1983).

* cited by examiner

Day 1, 10 µL

Day 2, 10 µL

Day 3, 10 µL

Day 4, 10 µL

METHOD OF ANALYZING ENZYME COMPOSITIONS WITH LIPOLYTIC, PROTEOLYTIC AND AMYLOLYTIC ACTIVITY

CROSS REFERENCE TO RELATED APPLICATIONS

This application claims priority from prior U.S. provisional patent application No. 60/490,510, filed Jul. 29, 2003.

BACKGROUND AND SUMMARY OF THE INVENTION

The present invention concerns a novel method to analyze identity, protein and/or peptide pattern and as well the stability of samples containing physiologically acceptable enzyme mixtures with lipolytic, proteolytic and amylolytic activity, but especially of mixtures of digestive enzymes such as pancreatin, in particular in the context of the manufacture of medicinal products comprising said enzyme mixtures, e.g. precipitated pancreatin or pancreatin mini-microspheres.

It is the object of the invention to provide new analytical method suitable for pharmaceutical preparations comprising mixtures of digestive enzymes such as pancreatin, in particular also in the context of the manufacture of medicinal products comprising said enzyme mixtures, e.g. pancreatin or pancreatin mini-microspheres. In particular it is the object to provide an analytical method suitable and reliable to be validated for pharmaceutical manufacturing for analyzing and determining the identity, protein and/or peptide pattern and as well the stability of said digestive enzyme samples. A further object is to provide said analytical method in conditions which are optimized for the analysis of pancreatin, in particular precipitated pancreatin or pancreatin mini-microspheres samples.

According to the invention, physiologically acceptable enzyme mixtures with lipolytic, proteolytic and amylolytic activity, such as suitable enzyme mixtures of microbial origin and/or especially mixtures of digestive enzymes of animal origin such as preferably pancreatin or pancreatin-like mixtures of digestive enzymes, are analyzed according to the analytical methods essentially described in this patent specification.

For the present invention, physiologically acceptable enzyme mixtures with lipolytic, proteolytic and amylolytic activity can be analyzed that are of any animal or microbiological origin. The enzyme mixtures with lipolytic, proteolytic and amylolytic activity analyzed by the method of the invention can be both of purely microbial origin, purely animal origin or may also be a mixture of enzymes of animal and microbial origin.

In one variant of the invention, therefore, the enzyme mixture used is of purely microbial origin. Especially enzymes produced by bacteria, i.e. by the *Bacillus* or *Pseudomonas* strains, or by fungal cultures such as molds, for example of the *Rhizopus* and *Aspergillus* strains, are especially suitable as microbial enzymes. Examples of such physiologically acceptable bacterial and/or mold fungi enzymes are already described in the state of the art, e.g. in connection with their synthesis and use for the treatment of maldigestion. Lipases may be derived from, for example, *Bacillus* or *Pseudomonas* strains, amylases and lipases from mold fungi, for example of the *Rhizopus* strain, and proteases, for example, also from *Aspergillus*.

One preferred variant of the invention, however, will involve the use of mixtures of digestive enzymes with lipoly- tic, proteolytic and amylolytic activity that in their properties closely resemble pancreatin. For the present invention, mixtures of digestive enzymes containing pancreatin and especially pancreatin itself are preferably used, and one or more microbial enzymes, i.e. enzymes synthesized by microorganisms, of the group of lipases, proteases and amylases may if desired be added to the pancreatin or the mixtures of digestive enzymes containing pancreatin. Most preferred the method according to the invention is suitable for analysis of precipitated pancreatin or pancreatin mini-microspheres samples.

Pancreatin is a known enzyme mixture with lipolytic, proteolytic and amylolytic activity which is available for example, under the trade name Creon®, in the form of granules, pellets or capsules containing enteric coated microspheres and is used medically for enzyme replacement, for example in pancreatic insufficiency, digestive insufficiency after stomach operations, liver and biliary diseases, cystic fibrosis and chronic pancreatitis. Pancreatin is generally obtained as a mixture of natural enzymes by extraction from porcine pancreas, for example according to the process described in U.S. Pat. No. 4,019,958 (=DE 25 12 746) and German patent no. DE 42 03 315, and is then converted into the desired galenical form in a manner known to the art. The pancreatic enzymes are usually administered orally in the form of solid preparations.

In one variant of the invention, the pharmaceutical preparations to be analyzed in accordance with the invention contain preferably pancreatin or mixtures of digestive enzymes containing pancreatin. These pharmaceutical preparations analyzed according to the invention can contain pancreatin or mixtures of digestive enzymes containing pancreatin and possibly in addition to pancreatin one or more physiologically acceptable enzymes from the group of lipases, proteases and amylases, of the kind that can be obtained from microorganisms. Microbial enzymes used in this supplement include especially the bacterially synthesized enzymes already mentioned above, for example by the *Bacillus* or *Pseudomonas* strains, or by fungal cultures such as mold fungi, for example of the *Rhizopus* or *Aspergillus* strains. The lipases contained in addition to the pancreatin or the mixtures of enzymes containing pancreatin may originate, for example, from *Bacillus* or *Pseudomonas* strains, added amylases and lipases from mold fungi, for example of the *Rhizopus* strain, and added proteases, for example, also from *Aspergillus*.

It has now been found that the physiologically acceptable enzyme mixtures with lipolytic, proteolytic and amylolytic activity such like pancreatin or non-animal sourced enzyme mixtures which can be obtained from microbial and/or animal sources and described with reference to this invention can be analyzed very efficiently according to the methods of the present invention. The invention provides a powerful and reliable (reproducible) method for e.g. analyzing and determining the identity, protein and/or peptide pattern and as well the stability of said digestive enzyme compositions or samples containing physiologically acceptable enzyme mixtures with lipolytic, proteolytic and amylolytic activity. It is evident to the skilled artisan that he may vary given parameters to a certain extent without loosing the overall functionality of the method according to the present invention; e.g. it may be wished to adapt the parameters indicated for performing the method in the following description, the examples, Tables and Figures by +/−10%, in particular by +/−5%.

Thus, the invention pertains to an analytical method for characterization and/or specification of protein samples containing physiologically acceptable digestive enzyme mixtures with lipolytic, proteolytic and amylolytic activity, which are used in the manufacture of pharmaceutical preparations for the treatment of disorders and/or disorders, by two-dimensional gel electrophoresis (2D GE), said method comprising:

(a) sample preparation by solving of an enzyme mixture sample in a solvent composition for gel electrophoresis comprising a specified solvent suitable to solve protein materials, an internal standard for quantification of proteins, and a protease inhibiting agent;

(b) an isoelectrical focussing step for defining the first dimension of the gel electrophoresis and applying a gradient for separation of the protein fractions;

(c) a subsequent pre-treatment step comprising re-buffering;

(d) transfer to the second dimension and separation by SDS-PAGE;

(e) fixing and staining of the gels resulting from step (d); and (f) densitometrical evaluation by fluorescence scanning.

The two-dimensional gel electrophoresis method is particularly suited for analyzing and determining the identity, protein and/or peptide pattern and as well the stability of said digestive enzyme compositions or samples containing physiologically acceptable enzyme mixtures with lipolytic, proteolytic and amylolytic activity, with molecular weights of the protein or peptide fractions from about 8 kDa (kilo Dalton) and above. In a variant the invention is particularly suited for analyzing and determining the identity, protein and/or peptide pattern and as well the stability of pancreatin, and in particular of precipitated pancreatin or pancreatin mini-microspheres. Parameters applicable in performing the method variants of the present invention are detailed below in the sections of the description pertaining to "Identification of spots using MALDI-TOF MS", "Stress Test Study for Precipitated Pancreatin", "Analytical Procedure for Determining Identity and Protein Pattern of Precipitated Pancreatin Samples by Two-Dimensional Gel Electrophporesis", and related Tables, and are further illustrated by the Figures given in the context of this invention.

For digestive enzyme samples, e.g. pancreation and in particular precipitated pancreatin or pancreatin mini-microspheres, with molecular weights of the protein or peptide fractions below about 8 kDa (kilo Dalton) the method may be supplemented according to a variant of the invention by additional application of analytical RP-HPLC method.

In an aspect the invention as defined above pertains to analysis of an enzyme mixture of microbially synthesized lipases, proteases and amylases. In another aspect the invention as defined above pertains to analysis of a pancreatin and/or a pancreatin-like mixture of digestive enzymes. In yet another aspect the invention as defined above pertains to analysis of a pancreatin a sample which is a precipitated pancreatin or a pancreatin mini-microspheres.

In a further aspect the invention as defined above pertains to an analytical method, wherein the solvent used in step (a) to dissolve the sample is a lysis buffer of 7M urea, 2M thiourea, 4% (w/v) CHAPS, 1% (w/v) DTT, and 0.5% Pharmalyte® at pH 3-10.

In a yet further aspect the invention as defined above pertains to an analytical method, wherein the internal standard for quantification of proteins used in step (a) is phosphorylase B, preferably rabbit phosphorylase B, or carbonic anhydrase, preferably bovine carbonic anhydrase.

In an additional aspect the invention as defined above pertains to an analytical method, wherein the protease inhibiting agent is Mini Complete and/or Pefabloc.

In a further aspect the invention as defined above pertains to an analytical method, wherein the solvent used in step (a) to dissolve the sample is Lp3 composed of 1.5 mg Mini Complete dissolved in 2 ml lysis buffer of 7M urea, 2M thiourea, 4% (w/v) CHAPS, 1% (w/v) DTT, and 0.5% Pharmalyte® at pH 3-10; and: 1 mg Pefabloc dissolved in 2 ml lysis buffer; in a ration 1:1 v/v.

The invention as defined above pertains also to an analytical two-dimensional gel electrophoresis method, wherein said method is applied for the characterization and quantification of protein and/or peptide fractions with a molecular weight above about 8 kD.

In a further aspect the invention as defined above pertains to an analytical method, which comprises determining the identity and/or the protein and/or peptide pattern of pancreatin, preferably of a precipitated pancreatin sample or of a pancreatin mini-microspheres sample.

In another aspect the invention as defined above pertains to an analytical method, which comprises the identification of protein and/or peptide spots using in addition MALDI-TOF-MS.

In one aspect the invention as defined above pertains to an analytical method, which is performed as a stress or stability test for determining the identity and/or the protein and/or peptide pattern of pancreatin, preferably of a precipitated pancreatin sample or of a pancreatin mini-microspheres sample, and impurities and/or degradants, and optionally comprising also the quantification said proteins, peptides, impurities and /or degradants.

In another aspect the invention as defined above pertains to an analytical method, wherein said method further comprises the characterization and quantification of low molecular weight protein and or peptide fractions with a molecular weight below about 8 kD by RP-HPLC.

In still another aspect the invention as defined above pertains also to a solvent composition suitable for characterization and/or specification of a sample of physiologically acceptable enzyme mixtures with lipolytic, proteolytic and amylolytic activity, which are used in the manufacture of pharmaceutical preparations for the treatment of disorders and/or disorders, by two-dimensional gel electrophoresis, comprising (a) as solvent suitable for gel electrophoresis and to solve protein materials which solvent is a lysis buffer of 7M urea, 2M thiourea, 4% (w/v) CHAPS, 1% (w/v) DTT, and 0.5% Pharmalyte® at pH 3-10;

(b) an internal standard for quantification of proteins; and (c) and a protease inhibiting agent.

In a variant of this solvent, the is a solvent composition, wherein the solvent to dissolve the sample is Lp3 composed of 1.5 mg Mini Complete dissolved in 2 ml lysis buffer of 7M urea, 2M thiourea, 4% (w/v) CHAPS, 1% (w/v) DTT, and 0.5% Pharmalyte® at pH 3-10; and: 1 mg Pefabloc dissolved in 2 ml lysis buffer; in a ration 1:1 v/v.

List of Some Abbreviations and/or Terms Used in the Following:

| | |
|---|---|
| mms | mini-microspheres (pancreatin mini-microspheres) |
| HCl | hydrochloric acid |
| API | active pharmaceutical ingredient |
| NDA | New Drug Application |
| FDA | Food and Drug Administration |
| MALDI-TOF MS | matrix assisted laser desorption and ionization mass spectroscopy |
| UTLIEF | ultrathin-layer isoelectric focusing |
| ESI-MS | electrospray ionization mass spectroscopy |

The analytical methods according to the invention, in particular after validation for pharmaceutical and regulatory purposes, are preferably intended to be used for characterization and specification setting of precipitated pancreatin and may also be applied to pancreatin enteric-coated minimicrospheres (pancreatin mini-microspheres).

For example, a product specification to be filed for the NDA for the active ingredient precipitated pancreatin and the dosage form pancreatin enteric-coated mms covers the items identification, purity, assay, gastric juice resistance and release of enzymes. State of the art identification is based on enzymatic assays which are used for determining the activity of the enzymes in both, the API and the dosage form. "Purity" also includes the determination of residual solvents (API, mms), fat (API), water (API, mms) and microbiological quality. For taking into account current FDA requirements and expectations based on Q6B Guidance "Specifications, Test Procedures and Acceptance Criteria for Biotechnological/Biological Products" more detailed characterization is regarded necessary for the drug substance and the dosage form with special attention to identification and quantification of different classes of enzymes, impurities and degradants from these enzymes. Results and methods from characterization will be selected for specification setting.

Therefore the present invention proposes for characterization and specification setting the use of two-dimensional gel electrophoresis (2D GE), because it was found that, since precipitated pancreatin is a complex mixture of different classes of constituents, two-dimensional gel-electrophoresis is expected to give by far the greatest selectivity for separation of peptides and proteins, i.e. different classes of enzymes, impurities and degradants of proteins. Furthermore, imaging of stained gels permits quantification of the constituents and comparison of the protein and/or peptide patterns in pancreatin samples, samples of precipitated pancreatin or pancreatin mini-microspheres. The present invention shows that identification of the most prominent spots can be performed by spot-picking and MALDI-TOF MS after tryptic digest.

In general, the separation by the two-dimensional gel electrophoresis method according to the present invention will be performed in the first dimension (step (b) isoelectric focussing) from aqueous buffered solutions of pancreatin samples or mms samples, after desalting of the sample, on gels with a pH gradient from 3 to 10 to cover a broad range of potential constituents or compounds. Focussing is performed on immobiline dry strips. An exemplary gradient to start with is tabulated below:

| Step (2D GE isoelectric focussing) | Voltage [V] up to aboout | Time [h] up to about |
|---|---|---|
| 1 | 150 | 4, preferably 1 |
| 2 | 300 | 4, preferably 1 |
| 3 | 600 | 3, preferably 1 |
| 4 | 1200 | 1 |
| 5 | 2400 | 1 |
| 6 | 3500 | 8, preferably 7.25 |

In general, the separation in the second dimension (step (d) SDS-PAGE) of the two-dimensional gel electrophoresis method according to the present invention will be performed on hand-made gels (for example under following condition: T=13%, C=3%) with e.g. a SDS-GLYCIN-TRIS buffer with an exemplary gradient as tabulated below:

| Step | Current [mA] about e.g. | Voltage [V] about e.g. |
|---|---|---|
| 1 | 80 | Max 45 |
| 2 | 150 | Max 200 |
| 3 | 10 | For security |

In general, staining is performed after fixation with for example ethanol/acetic acid mixture with a fluorescent dye and subsequent destaining in for example ethanol/acetic acid. After washing with water, densitometric scanning is performed. Afterwards, staining with for example colloidal Coomassie blue is performed for identification by MALDI-TOF MS. For this purpose, spots will be picked from the gel and subjected to a tryptic digest. Peptides are eluted from the gel for example with acetonitrile/0.1% TFA and purification on a C18 ZipTip Column. After co-crystallization with 2,5-dihydroxy benzoic acid, the extracts are pipetted on the target plate.

As an example to illustrate the applicability and usefulness of the present invention in the analytical method three batches each of three species of precipitated pancreatin (glands from different countries and different manufacturing processes), including Pancreatin SPL 85 were selected. One sample of each batch was applied on a gel, for one batch of each species the analysis was performed threefold to check reproducibility of the precipitation step, the sample preparation and the separation. The spots were quantified and identification of characteristic spots was performed.

As an example to illustrate the applicability and usefulness of the present invention in stability testing, the same batches as used before to illustrate the applicability and usefulness were subjected to stress conditions (temperature, humidity, light) to determine any loss of activity and then to analyze or investigate also differences and, if applicable, identify potential degradants.

As indicated above, for digestive enzyme samples, e.g. pancreatin and in particular precipitated pancreatin or pancreatin mini-microspheres, with molecular weights of the protein or peptide fractions below about 8 kDa (kilo Dalton) the method may be supplemented according to a variant of the invention by additional application of analytical RP-HPLC method. Parameters applicable in performing the RP-HPLC method variants of the present invention are detailed below in the section of the description pertaining to "Feasibility of RP-HPLC with MALDI-TOF-MS for Analysis of Pancreatin".

Identification of spots using MALDI-TOF MS", "Stress Test Study for Precipitated Pancreatin", "Analytical Procedure for Determining Identity and Protein Pattern of Precipitated Pancreatin Samples by Two-Dimensional Gel Electrophoresis", and related Tables, and are further illustrated by the Figures given in the context of this invention.

HPLC is a widely automated, well reproducible, highly selective method which is widely used for routine analysis, also in protein analysis. Quantification of compounds is easy and identification of peaks can be performed by LC-ESI-MS. Peptides of lower molecular mass and other low-molecular compounds can be detected and identified so that the method is complementary to e.g. two-dimensional gel electrophoresis or SDS-PAGE. It can therefore be used in particular for fingerprinting, identification purposes and quantification of enzyme classes, impurities and degradants.

Usually the HPLC method involves for example an agilent HPLC-equipment consisting of: Autosampler G 1313A;

Quat. pump G 1311A; UV-detector G 1314A; Vacuum degasser G 1322A; HP Column Oven G 1316A; 1100 control module G 1323A; LAN-interface 35900E; and ChemServer; or an equivalent system. A typical HPLC column may be as an example a MODULO O-CART QS UPTISPHERE 5 WRP, Interchim (UP5WRP$15QS) with a stationary phase of RP 18, 5.0 μm, tubing material of stainless steel with a length of 150 mm and an internal diameter of 3.0 mm; or a comparable equivalent HPLC column. The RP 18, 5.0 μm phase is beneficial for example, as it is possible to operate with 100% water, and it is suitable for proteins and peptides. Further examples for suitable columns are e.g. Polaris 5 μm C18-A 150×4.6 mm obtainable from Varian B. V., Middelburg, The Netherlands (article order no. A2000150X046); or e.g. Cogent Bidentate, C( (Octyl), 4 μm, 300 A, 150×4.6 mm from MicroSolv Technology Corporation, Long Branch, N.J. 07740, USA.

The HPLC method may be operated under following exemplary conditions:

| Operating mode<br>Mobile phase | Gradient HPLC |
|---|---|
| mobile phase A | water/TFA 0.05% (v/v) |
| mobile phase B | acetonitrile/TFA 0.05% (v/v) |

| Gradient | | | |
|---|---|---|---|
| Time [min] | % A | % B | |
| 0 | 100 | 0 | linear gradient to |
| 75 | 10 | 90 | linear gradient to |
| 75.1 | 100 | 0 | isocratic |
| 80 | 100 | 0 | equilibration |

Flow rate 1.0 ml/min
Period of analysis 75 min
Temperature 20 ± 5.0° C.
Injection volume 10 μl For detection, for example, a UV-detector may be used at a wavelength of 214 nm Identification of Spots Using MALDI-TOF MS According to one aspect of the invention the analytical method comprises the identification of protein spots from a two-dimensional gel, e.g. for a sample of precipitated pancreatin. This identification of spots using MALDI-TOF MS is described in more detail in the following paragraphs. The method procedures are described further below in more detail for two-dimensional gel electrophoresis as well as for MALDI-TOF MS. The protein characterization is performed by establishing a peptide mass fingerprint from a wet gel obtained by performing a two-dimensional gel method, and by additionally applying MALDI-MS/MS for spots which were not unambiguously identified.

Peptide Mass Fingerprint:

For peptide mass fingerprinting (PMF) the respective spots are manually cut out of the wet gel using a manipulated pipette tip with a diameter of 0.2 cm. Each spot is then transferred into a single tube (0.5 ml). The Coomassie blue-stained spots are destained using a special washing procedure: 1.100 μl of 10 mM ammoniumhydrogen carbonate, shaking for 5 minutes, 2.10 mM ammoniumhydrogen carbonate, 50% acetonitrile, shaking for 5 minutes. This procedure has to be repeated at least 3 times or until all spots are completely colorless. After the last washing step 5 μl of acetonitrile is added to each tube. When the spots are white, 2-6 μl of digestion buffer can be added, depending on the amount of gel within the tubes. The digestion buffer is 10 mM ammoniumhydrogen carbonate containing 0.01 μg/μl modified bovine trypsin (Roche Diagnostics, Basel, Switzerland). The digestion is performed over night at 37° C.

After digestion the supernatant is removed, leaving the gel matrix in the tubes. If there is no supernatant left 5-μl of an extraction medium (1% TFA, 50% acetonitrile) should be added. After 10 minutes of ultrasonification in a sonification bath the tubes are transferred to a speedvac to remove the acetonitrile. Then the peptides are enriched and the samples are desalted by using a C18 ZipTip (Millipore, USA) according to the manufacturer's instructions. The extracted mixtures can now be transferred onto a MALDI-MS target (Applied Biosystems). A quantity of 0.1 μl of the sample is mixed with 0.1 μl of DHBS matrix (2,5 Dihydroxybenzoic acid: 2 Hydroxy-5 methoxy-benzoic acid 9:1). The target is then measured by a MALDI mass spectrometer (Voyager STR, Applied Biosystems, Foster City, Calif., USA). As mass range in reflector mode 600-4200 Dalton (Da) was used. The low molecular weight range (<600 Da) is difficult to detect because of matrix effects.

The PMF spectra are labeled and internally calibrated onto 2 masses of known autotryptic peptides (805.42 Da; 2163.05 Da). The calibrated spectrum normally has an accuracy of less than 50 ppm.

The data base searches for the PMFs is performed using the software ProFound (Genomic Solutions, USA). Significant hits are reached when the gap between hit 1 and hit 2 is at least e-04 and the most intense masses can be explained or if the sequence coverage is relatively high (>30%).

The results of identification are tabulated below in Table A, and FIG. 1 shows a two-dimensional gel obtained with the labeling of identified spots from precipitated pancreatin.

Furthermore, FIG. 2 depicts the high reproducibility of the method according to the present invention. Three gels were prepared of a single sample of precipitated pancreatin on four different days.

MALDI-MS/MS:

Protein spots that could not be identified unambiguously by PMF were chosen for MALDI-MS/MS using a Proteomics Analyzer 4700 (Applied Biosystems, Framingham, Calif., USA). For this purpose, peptides with certain peak intensity were chosen and fragmented to obtain sequence information. The obtained fragment spectra were used to search the NCBI database (http://www.ncbi.nih.gov/), National Center for Biotechnology Information, National Library of Medicine, Building 38A, Bethesda, Md. 20894, USA using the Mascot software (Matrixscience, London, UK). Spectra exceeding a certain Mascot score are significant. In questionable cases a manual control is performed. Table A shows the results obtained by MALDI-MS/MS.

Stress Test Study for Precipitated Pancreatin

According to a further aspect of the invention the two-dimensional gel electrophoresis method is used for the monitoring of degradation processes and/or monitoring of the stability samples of precipitated pancreatin. This stability testing is described in more detail in the following test report pertaining to a stress (stability) test for precipitated pancreatin.

According to another aspect of the invention in a stress test the suitability of a two-dimensional gel electrophoresis (2D GE) method was investigated for (a) stability testing when applied to precipitated pancreatin, (b) for locating potential degradation products formed during stress testing, and (c) for identifying spots which show degradation. The study revealed significant changes of some spots already identified, which are comparable for both types of precipitated pancreatin included in the study. The method is therefore regarded stability indicating.

To evaluate the suitability of the two-dimensional gel electrophoresis method for characterization of precipitated pancreatin, samples of precipitated pancreatin were put on storage under stress-testing conditions and investigated according to the methods of the present invention. Aliquots of these samples were examined by two-dimensional gel electrophoresis to determine the duration required to perform stress-testing and to look for spots which can be associated to degradation products of pancreatin.

The stress testing was performed according to the analytical procedure "Identity and Protein Pattern by Two-Dimensional Gel Electrophoresis" as described in detail below. For the stress testing the following samples were used:

| Sample | Storage Condition | Time Points/days |
|---|---|---|
| Pankreatin N | 40°/75% | 0. 16. 32 |
| Pancreatin SPL 85 | 40°/75% | 0. 15. 28 |

Quantities of 20 g of precipitated pancreatin were filled in Petri dishes and were covered with a second Petri dish. The sample was put on storage at 40° C./75% r.h. Samples of 100 mg were harvested in the beginning and after 1, 2, 4, 8, 16 and 32 days. Samples pulled after 0, 16 and 32 days were examined by 2D GE. All the samples were stored in a deep freeze. i.e. below −15° C. protected from light and humidity till they were used for investigation.

The results are shown in the Tables A to I and in the FIGS. 1 to 7 which depict the 2D gels obtained in the stress stability testing of precipitated pancreatin samples. The content of said Tables and Figures is summarized as follows:

Contents of Tables A to I:
Table A Spots from 2D-GE with Accession No. to NCBI Database (see also FIG. 1)
Table B Spot intensities for Pancreatin Batch 1 (t=0 and 16 days) with average and standard deviation and regulation of spot vs. t0
Table C Spot intensities for Pancreatin Batch 1 (t=0 and 16 days) with average and standard deviation and regulation of spot vs. t0
Table D Spot intensities for Pancreatin Batch 1 (t=32 days) with average and standard deviation and regulation of spot vs. t0
Table E Spot intensities for Pancreatin Batch 1 (t=32 days) with average and standard deviation and regulation of spot vs. t0
Table F Spot intensities for Pancreatin Batch 2 (t=0 and 15 days) with average and standard deviation and regulation of spot vs. t0
Table G Spot intensities for Pancreatin Batch 2 (t=0 and 15 days) with average and standard deviation and regulation of spot vs. t0
Table H Spot intensities for Pancreatin Batch 2 (t=32 days) with average and standard deviation and regulation of spot vs. t0
Table I Spot intensities for Pancreatin Batch 2 (t=32 days) with average and standard deviation and regulation of spot vs. t0

BRIEF DESCRIPTION OF THE DRAWINGS

The invention will be described in further detail hereinafter with reference to the accompanying drawing figures in which.

Figure 1:
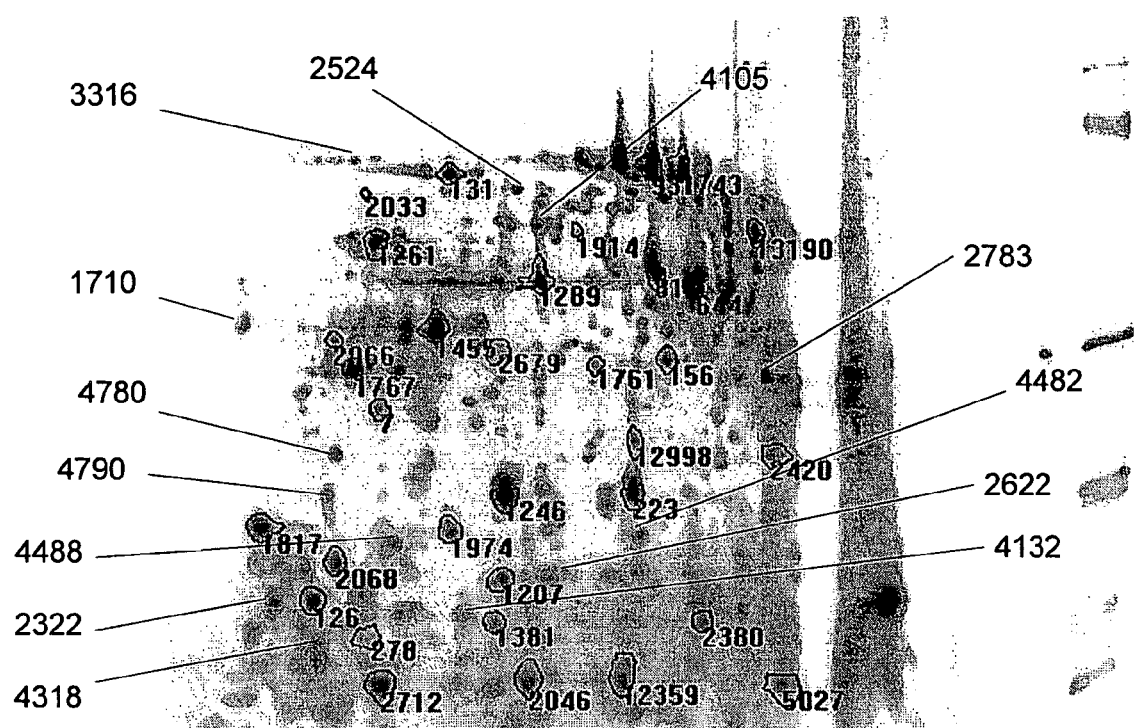
FIG. 1 2D-Gel obtained with Precipitated Pancreatin with identified spots labeled (Cf. also Data in Table J and K)
FIG. 2 Reproducibility of the 2D-gel method with a single sample of precipitated pancreatin; 3 gels performed on 4 different days (IPG 3-10NL, fluorescence dying; external standard carbonic anhydrase, applied quantity 320 ng)
FIG. 3 2D-Gel obtained for Pancreatin batch 1 after Stress Testing (Sypro Ruby)
FIG. 4 2D-Gels obtained for Pancreatin Batch 2 after Stress Testing (Sypro Ruby)
FIG. 5 Averaged gels (n=3) calculated for Pancreatin Batch 1
FIG. 6 Averaged Gels (n=3) calculated for Pancreatin Batch 2
FIG. 7 2D Gel of Precipitated Pancreatin with addition of two internal marker proteins Phosphorylase B and Carboanhydrase, obtained as described in the section in the description pertaining to the Analytical Procedure "Identity and Protein Pattern"
FIG. 8 Typical Chromatogram of Precipitated Pancreatin, Batch 1.
Figure 2:
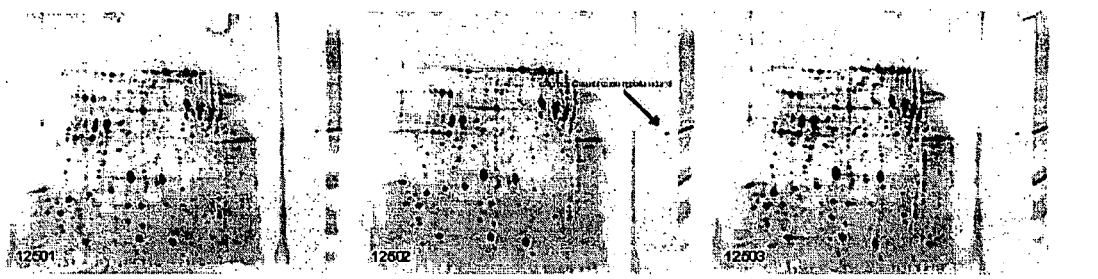
Figure 2:
Figure 2:
Figure 2:
Figure 3:
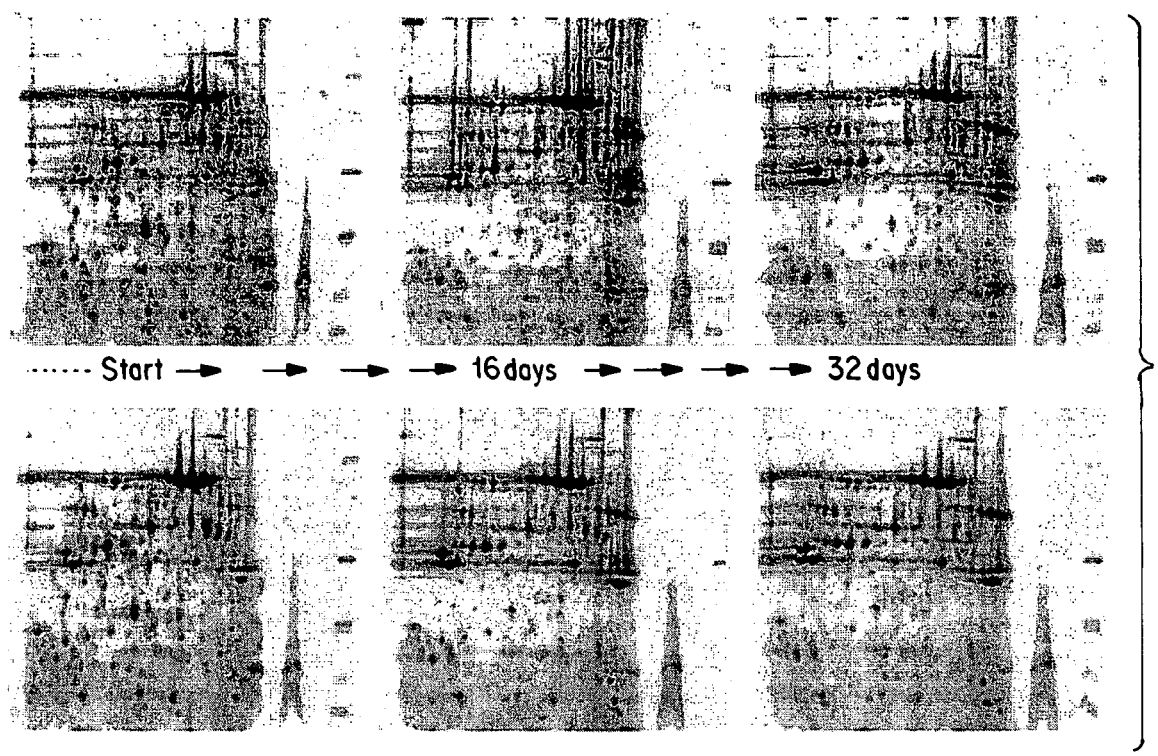
Figure 4:
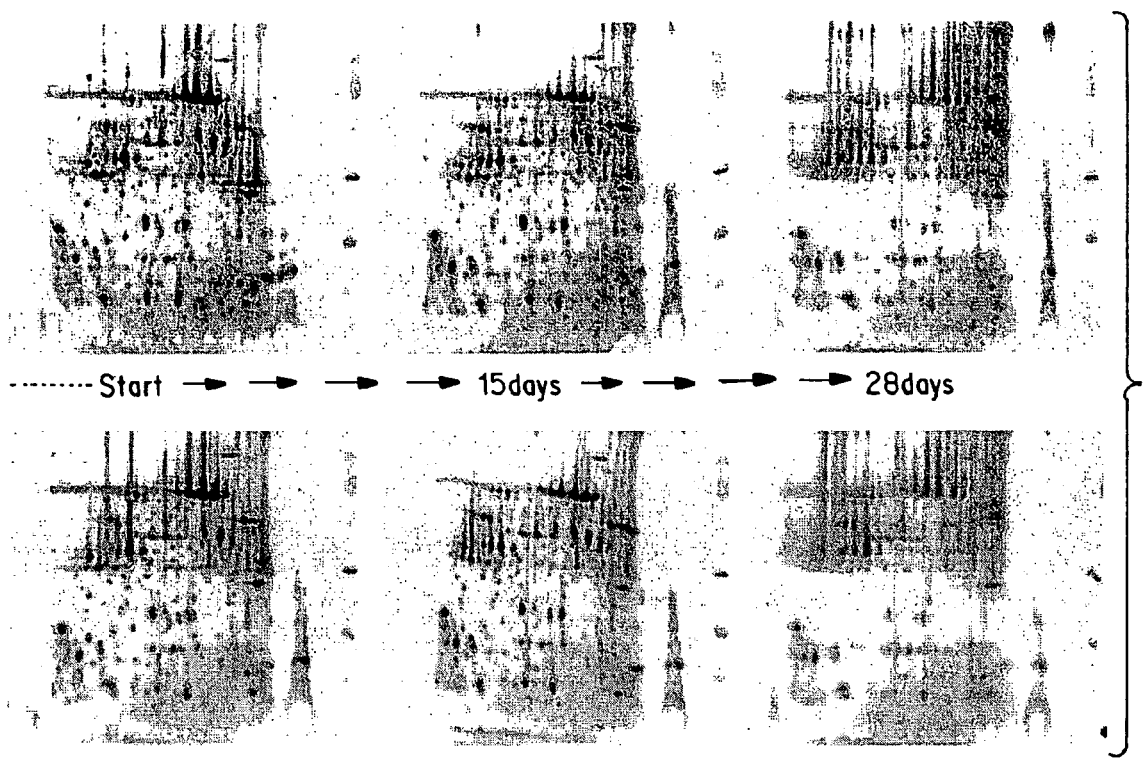
Figure 5:
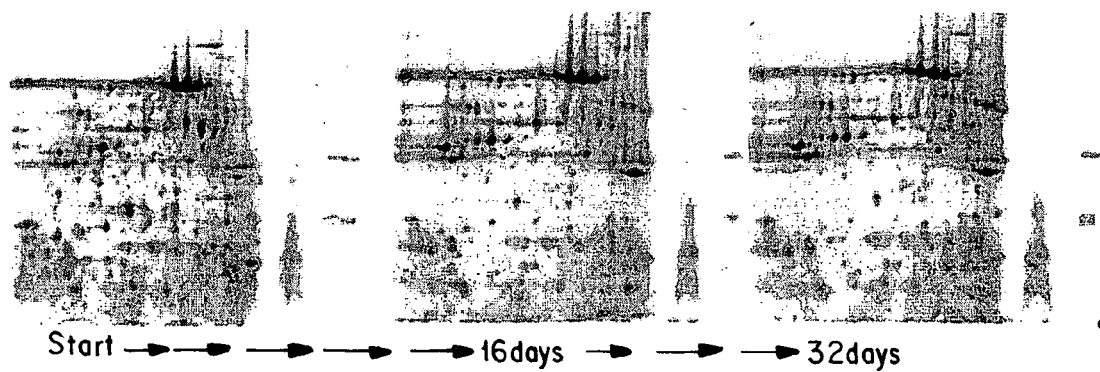
Figure 6:
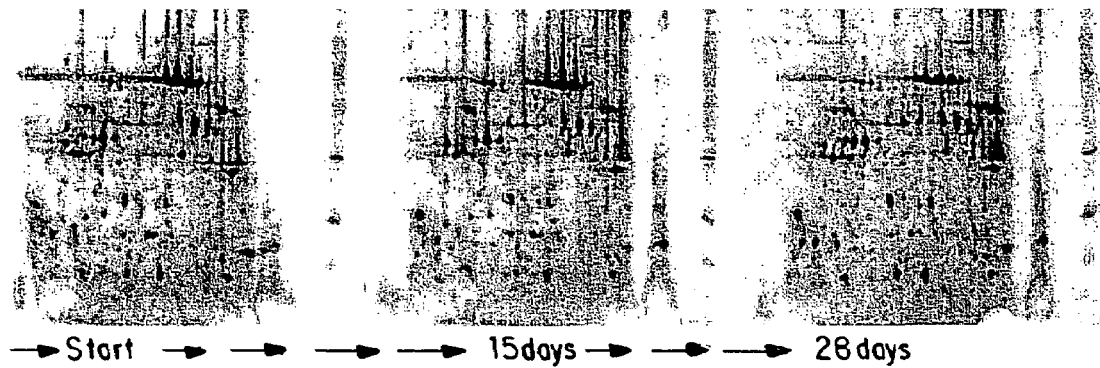

ANALYTICAL PROCEDURE FOR DETERMINING "IDENTITY AND PROTEIN PATTERN OF PRECIPITATED PANCREATIN SAMPLES BY 2D GEL ELECTROPHORESIS

According to one aspect of the invention the 2D gel electrophoresis method is used as analytical procedure for determining the identity and the protein pattern of precipitated pancreatin samples by 2D gel electrophoresis. This procedure is described herein in more detail using the following abbreviations:
CHAPS 3-(3-cholamidopropyl)dimethylammonio-1-propane-sulfonate
DTT Dithiothreitol
TRIS Tris(hydroxymethyl)-aminomethane
APS Ammonium persulfate
TEMED N,N,N',N'-tetramethylethylenediamine
SDS Sodium dodecylsulfate Description of the Two-Dimensional Gel Electrophoresis Method Applied:

Two-dimensional gel electrophoresis (2D GE) separation technique (O'Farrell P H, J. Biol. Chem. 250: 4007-4021 (1975)) takes advantage of the electrophoretic mobilities of individual constituents of a complex mixture of proteins, fractionating according to charge (pI) by isoelectric focusing (IEF) in the first dimension and according to size (Mr) by SDS-PAGE in the second dimension.

In general the electrophoresis is performed according to the European Pharmacopoia (Ph. Eur. 2.2.31), and in this context the term "water" without qualification means double distilled or deionized water or water of an equivalent quality. In the method the following Materials and Reagents are applied:

Acetonitrile, e.g. Merck, Art.No. 1033530220
Acrylamid-Solution, e.g. Serva, Art.No. 10688.02
Agarose, e.g. VWR International, Art.No. 1.16802.0025
Ammonium persulfate, e.g. Serva, Art.No. 13 375.01
Bromphenolblue, e.g. VWR International, Art.No. 1.08122.0005
2-Butanol, e.g.:VWR International, Art.No. 8.22263.1000
CHAPS, e.g. Roth, Art.No. 1479.2
DTT, 1,4-Dithiothreitol, e.g. Roth, Art.No. 6908.2
Electrode Paper, e.g. Amersham Biosciences, Art.No. 80-1106-19
Electrode paper stripes, e.g. Amersham Biosciences, Art.No. 18-1004-40
Ethanol, e.g. VWR International, Art.No. TC212-9025
Acetic Acid, e.g. Roth, Art.No. 3738.2
Immobiline Dry Strips, pH 3-10NL, e.g. Amersham Biosciences, Art.No. 17-1235-01
Glycerine, e.g. Serva, Art.No. 23176
Glycine, e.g. Roth, Art.No. 3908.3
Urea, e.g. Roche Diagnostics, Art.No. 1 685 902
Lodacetamide, e.g. Sigma, Art.No. I-6125
Pharmalyte™ 3-10, Amersham Biosciences, Art.No. 17-0456-01
Protein Test Mixture 4, Serva, Art.No. 39208.01
Protein Test Mixture 5, Serva, Art.No. 39209.01
Roti-Blue®-Concentrate, Art.No., A152.1
Sample Cups, e.g. Amersham Biosciences, Art.No. 18-1004-35
SDS, Sodium dodecyl sulfate, e.g. Serva, Art.No. 20 763.02
Silicon Oil, e.g. Serva, Art.No. 35132
TEMED, e.g. Bio-Rad, Art.No. 161-0800
Thiourea, e.g. Fluka, Art.No. 88810
TRIS, for Electrode Buffer, e.g. Roth, Art.No. 4855.2
TRIS, for all other solutions, e.g. Bio-Rad, Art.No. 161-0719

The following solutions also are used in the method:
(1) Lysis Buffer:
  7 M Urea, 2 M Thiourea, 4% (w/v) CHAPS, 1% (w/v) DTT, 0.5% Pharmalyte™ pH 3-10
(2) Solvent for Sample LP3:
  1.5 mg Mini Complete dissolved in 2 ml of Lysis buffer 1:1 mg Pefabloc dissolved in 2 ml Lysis buffer (1:1 v/v)
(3) Rehydration Solution:
  6 M Urea, 2 M Thiourea, 4% CHAPS, 0.2% DTT, 0.2% Pharmalyte™ pH 3-10, some Bromphenolblue
(4) Gel Solution (T=13%. C=3%):
  75 g Glycerol, 425 mL water, 375 mL Separation Gel Buffer (5), 630 mL Acrylamidlösung
(5) Separation Gel Buffer:
  Dissolved 181.66 g TRIS, 4 g SDS in 900 ml of water and adjusted with hydrochloric acid R to a pH of 8.8, adjusted to a volume of 1000 ml using water
(6) APS-Solution:
  10% (w/v) Ammonium persulfate in water
(7) Glycerol Solution:
  50% (v/v) Glycerol in water, add some bromophenolblue
(8) Butanol Saturated with Water:
  2-Butanol, stored above water
(9) Electrode Buffer:
  19.9 g SDS, 299.6 g Glycin, 58.0 g TRIS are dissolved in 20 l water
(10) DTT-Solution:
  1% DTT in Equilibration Buffer
(11) Lodacetamide Solution:
  4% Lodacetamide dissolved in Equilibration Buffer
(12) Equilibration Buffer:
  Dissolve 30% Glycerol, 6M Urea, 4% SDS and 33.40 mL Separation Gel buffer (5) in water and adjust the volume to 1000 ml
(13) Agarose Solution:
  Dissolve 300 mg Agarose and some Bromophenolblue in 60 ml of Buffer(9) and boil until the solution becomes clear
(14) Protein Standard Solution:
  10 mg each of Protein Test Mixture 4 and 5 are dissolved in 1 mL Lysispuffer (1). The solution is colored by adding a small qty. of bromophenol blue. Molecular weights of the proteins are: 6.5 kDa, 12.5 kDa, 21 kDa, 29 kDa, 45 kDa, 67 kDa, 97.4 kDa.
(15) Ethanol/Acetic Acid Mixture:
  7% Acetic Acid, 10% Ethanol
(16) Sypro Ruby Solution, Biorad
(17) Coomassie Solution:
  Add 180 mL of water and 60 mL of methanol to 60 mL Roti-Blue®-Concentrate while stirring Description of Pefabloc SC:
  AEBSF 4-(2-Aminoethyl)-benzenesulfonyl fluoride hydrochloride; it has the following characteristics: homogeneous in TLC; formula: $C_8H_{10}NO_2SF \times HCl$; molecular weight: $M_r = 239.5$; specific, potent, and irreversible inhibitor of serine proteases. The inhibitory activity of Pefabloc SC is comparable to PMSF or DFP, however, it is non-toxic. Suggested Starting Concentration is 0.1-1.0 mg/ml (0.4-4 mM).

Description of Mini Complete:
  Complete Mini Protease Inhibitor Cocktail Tablets; it has the following product profile: specificity of inhibitor; mixture of several protease inhibitors with broad inhibitory specificity. Inhibits serine, cysteine, and metalloproteases, as well as calpains. Use for extracts from tissues or cells, including animals, plants, bacteria, yeast, and fungi. Contains both reversible and irreversible proteases. Solubility/Stability: soluble in aqueous buffers, or to be added directly to extraction media. Alternatively, prepare 7×stock solutions in 1.5 ml water or 100 mM phosphate buffer, pH 7.0. Stock solution is stable for 1-2 weeks at 4° C. or at least 12 weeks at −20° C. All inhibitors in Complete can be removed via dialysis. Use of a membrane with cutoff >10 kDa is recommended. Complete can be used in thiol-containing solutions at room temperature. Suggested starting concentration: dissolve one tablet in 10 ml aqueous buffer or water. If very high proteolytic activity is present, use one tablet for 7 ml buffer.

The method is performed with the following Equipment or with suitable equivalent equipment known to the skilled artisan:
  Ultrasonifier: Bandelin electronics, Sonoplus, HD 2070
  Reswelling Tray: Immobiline DryStrip Reswelling Tray for 7-18 cm IPG strips; Art.No. 80-6371-84, Amersham Biosciences
  Electrophoresis Apparatus: Multiphor II, Art.No. 18-1018-06, Immobiline Dry Strip Kit, Art.No. 18-1004-30, Amersham Biosciences
  Gel caster: DALT Multiple Gel Caster, Art. No. 80-6330-61, Amersham Biosciences
  Casting Cassettes: Dalt Gel Cassette, Art. No. 80-6067-27, Amersham Biosciences
  Separation Sheets: Separator Sheets, Art. No. 80-6436-63, Amersham Biosciences
  Hoefer Dalt-Separation Chamber: IsoDalt Gel Electrophoresis System ID 440-230V; Art.No. 80-6068-98, Amersham Biosciences
  Thermostating unit: MultiTemp III Thermostatic Circulator, Art.No. 18-1102-78, Amersham Biosciences Electrophoresis Power Supply: EPS 3501 XL Power Supply, Art.No. 18-1130-05, Amersham Biosciences Fluorescence Scanner FLA3000 (Raytest)

ProteomWeaver 2.2 (Definiens AG, 80339 Munchen, Germany)

(A) Sample Preparation 10 mg of the sample of precipitated pancreatin to be examined is dissolved in 500 µl of Lp3. After shaking for 5 min at ambient temperature, the suspension is centrifuged. The clear supernatant is used for determination of the protein content (Bradford). Two different proteins are used as internal standards, i.e. phosphorylase b (from rabbit) and bovine carbonic anhydrase. These standards are added to the sample solution before separation in the first dimension is performed. To varying amounts (5-15 µl) of the clear supernatant 2 µl of internal standard solution 1 and 6.7 µl of internal standard solution 2 are added.

Preparation of Internal Standard Solution 1 (Phosphorylase b):

A solution of phosphorylase b is prepared—lyophilized (Sigma, Prod.No.: P-6635) in Lysis buffer 3 with a concentration of 1 µg/µl by shaking at 20° C. for 30 minutes.

Preparation of Internal Standard Solution 2 (Carbonic Anhydrase):

A solution of carbonic anhydrase is prepared—lyophilized (Sigma, Prod.No.: P-6403) in Lysis buffer 3 with a concentration of 0.03 µg/µl by shaking at 20° C. for 30 minutes.

(B) Rehydration of Immobiline Dry Strips

The ready-cut IPG-strips (Immmobiline Dry Strips (T=4%, C=2,7%, pH 3-10NL) are delivered in a dried and frozen status. Before use the strips are rehydrated over night in the Reswelling Tray. For 18 cm strips 350 µL of Rehydration Solution (3) are used.

(C) Isoelectric Focussing (First Dimension)

(C.1) Preparation of Rehydrated Immobiline Dry Strips:

The cooling block of the electrofocusing chamber is thermostated to 20° C. The rehydrated stripes are dipped into water and are placed, gel up, on a sheet of water saturated filter paper (electrode paper). Wet a second sheet of filter paper with water, blot it to remove excess water and put it onto the surface of the IPG gel strips. Blot them gently for a few seconds to remove excess rehydration solution.

(C.2) The Procedure is Performed According to the Following Steps 1 to 13:

1. The cooling plate is placed into the Multiphor II Electrophoresis unit. 5 ml of silicone oil is pipetted onto the cooling plate followed by positioning of the Immobiline DryStrip tray on the cooling plate. Trapping large air bubbles between the tray and the cooling plate is to be avoided.
2. Connection of the electrode leads on the tray to the Multiphor II unit.
3. Pouring of about 5 ml of silicone oil into the tray.
4. Placing of the Immobiline strip aligner into the tray on top of the oil.
5. Transferring of the rehydrated IPG gel strips (gel-side up and acidic end towards the anode) into adjacent grooves of the aligner in the tray. Aligning of the strips such that the anodic gel edges are lined up.
6. Cutting of two IEF electrode strips or paper strips prepared from 2 mm thick filter paper (e.g. MN 440, Macherey & Nagel, Germany) to a length corresponding to the width of all IPG gel strips lying in the tray. Soak the electrode strips with water, removing excessive moisture by blotting with filter paper and placing the moistened IEF electrode strips on top of the aligned strips near the cathode and anode.
7. Positioning of the electrodes and pressing them gently down on top of the IEF electrode strips.
8. Putting the sample cups on the sample cup bar. Placing of the cups high enough on the bar to avoid touching the gel surface. The sample cup bar is put in a position that there is a distance of a few millimeters between the sample cups and the anode (or cathode, in case of cathodic sample application).
9. Moving of the sample cups into position, one sample cup above each IPG gel strip, and finally pressing down the sample cups to ensure good contact with each strip.
10. Once the sample cups are properly positioned, about 50 ml of silicone oil is poured into the tray so that the IPG gel strips are completely covered. If the oil leaks into the sample cups, suck the oil out, sample cups are re-adjusted and checked for leakage again. Filling up each sample cup with a few drops of silicone oil.
11. The samples are pipetted into the cups by underlaying, and again watched for leakage.
12. The lid of the Multiphor II electrophoresis chamber is closed and the run according to the parameters (running conditions) given in the table below is started. For improved sample entry, voltage is limited to low voltages (150-300 V) for the first few hours. Then it is continued to the steady state.

| Running Conditions for pH 3-10NL: | | |
| --- | --- | --- |
| Step | Voltage [V] | Time [h] |
| 1 | 150 | 1 |
| 2 | 300 | 1 |
| 3 | 600 | 1 |
| 4 | 1200 | 1 |
| 5 | 2400 | 1 |
| 6 | 3500 | 7.25 |

13. When the IEF run is completed, the electrodes, sample cup bar and IEF electrode strips are removed from the tray. Clean forceps are use and the IPG gel strips are removed from the tray. Thoes IPG gel strips which are not used immediately for second dimension run and/or are kept for further reference are stored between two sheets of plastic film at −78° C. up to several months.

(D) Casting of Gels for Second Dimension (SDS PAGE)

One day before the casting of gels 1.5 liters of gel solution are prepared and degassed and filtered. The solution is stored overnight at 4° C. in a tightly closed flask. The reservoir of the casting chamber is closed with a funnel. 125 ml of glycerol solution are filled in. Immediately before casting 75 µl TEMED and 8 ml of APS-solution are added to the gel solution, while stirring and the solution is filled into the casting chamber. After complete transfer of the gel solution, the funnel is removed and glycerol solution from the reservoir is added. The gel solution is now located in the casting cassettes of the casting chamber only. The gels are immediately overlayed with butanol, saturated with water, and the gels are polymerized for three hours.

(E) Second Dimension (SDS-PAGE)

The SDS-PAGE procedure is performed according to the following steps 1 to 11:

1. The electrophoresis chamber is filled with Electrode buffer (9) and turned on cooling (13° C.). The gels in the casting chamber are overlayed with some water until usage.
2. For each gel, a small strip of filtration paper is soaked with 5 μl of a protein standard solution
3. The SDS gel is supported in a vertical position to facilitate the application of the first dimension IPG strips.
4. The IPG gel strips are equilibrated as follows: The focused IPG gel strips are taken out of the freezer and they are placed into individual test tubes. 10 ml of equilibration buffer is added. The test tubes are sealed with Parafilm, they are rocked for 10 min on a shaker and then the equilibration buffer is poured off. 10 ml of iodoacetamide solution is added to the test tube as above and equilibrate for another 10 min on a rocker.
5. After the second equilibration, the IPG gel strip is rinsed with electrode buffer for a few seconds.
6. Excess water is removed from the gel, the IPG gel strip and the filtration paper with protein standard solution are placed besides on top of an SDS gel and overlayed with hot agarose solution (75° C.). Carefully the IPG strip is pressed with a spatula onto the surface of the SDS gel to achieve complete contact. The agarose is allowed to solidify for at least 5 min. This procedure is repeated for the remaining IPG strips.
7. The gel cassettes are inserted into the electrophoresis apparatus and the electrophoresis is started.
8. The SDS-PAGE gels are run overnight as illustrated in the table below. Step 1 lasts for 50 Vh.

| Running conditions for second dimension (SDS-PAGE) | | | |
|---|---|---|---|
| Step | Current [mA] | Voltage [V] | [Vh] |
| 1 | 80 | max. 45 | 50 |
| 2 | 150 | max. 200 | Variable, see step 9 |
| 3 | 10 | Last step for security | |

9. The run is terminated when the bromophenol blue tracking dye has reached the lower end of the gel.
10. The cassettes are carefully opened with a spatula, and a spatula is also used to remove the agarose overlay from the polyacrylamide gel.
11. The gels are removed from cassette holders and then immersed in water to remove the gel off the glass plate. Then it is continued with fixing, protein staining or blotting.

(F) Fixing and Staining of Gels

Each gel is fixed separately. Fixing is carried out with 350 ml of ethanol/acetic acid mixture for 30 minutes. Staining is performed for 3 hours with SyproRuby-solution (350 ml) protected from light. Destaining of the background is accomplished with 350 ml of Ethanol/Acetic acid mixture for 30 minutes, protected from light. Before scanning, the gel is washed two times with water. If required, the gel is stained after scanning with colloidal Coomassie-solution over night. The coloured gels are shaken the next day in water. When the background is almost destained, scanning can be performed using the visual scanner.

Evaluation of the Analytical 2D Gel Electrophoresis Procedure

A typical 2D gel obtained with precipitated pancreatin is shown in FIG. 1 with identified spots labeled. All obtained images for evaluation of the 2D-gels are measured with a Fluorescence Scanner FLA3000 (Raytest). The gels are scanned as 16-bit files with a pixel size of 100μ. Excitation wavelength is 473 nm.

The tiff-files are evaluated with ProteomWeaver 2.2 (Definiens). An experiment is performed by arranging the images in adequate groups. Then a spot detection over all gels is done, according to the algorithm of the software. The used settings for detection are default settings and are sufficient for almost all observable spots in the gels. After spot detection, all individual gels are rechecked manually to make sure that incorrect detection is reduced to a minimum. At the same time when the spot detection takes place an automatic quantification of the spots is performed by the software, and the quantities are normalized throughout the whole experiment to facilitate a comparison of spot identities of the different spots in the gels. This normalization process is independent of the number of gels in the experiment and can also be performed for those gels which are integrated into the experiment at different time points. A matching process is then started which assigns same spot identities to the identical spots throughout the gels.

Figure 7:
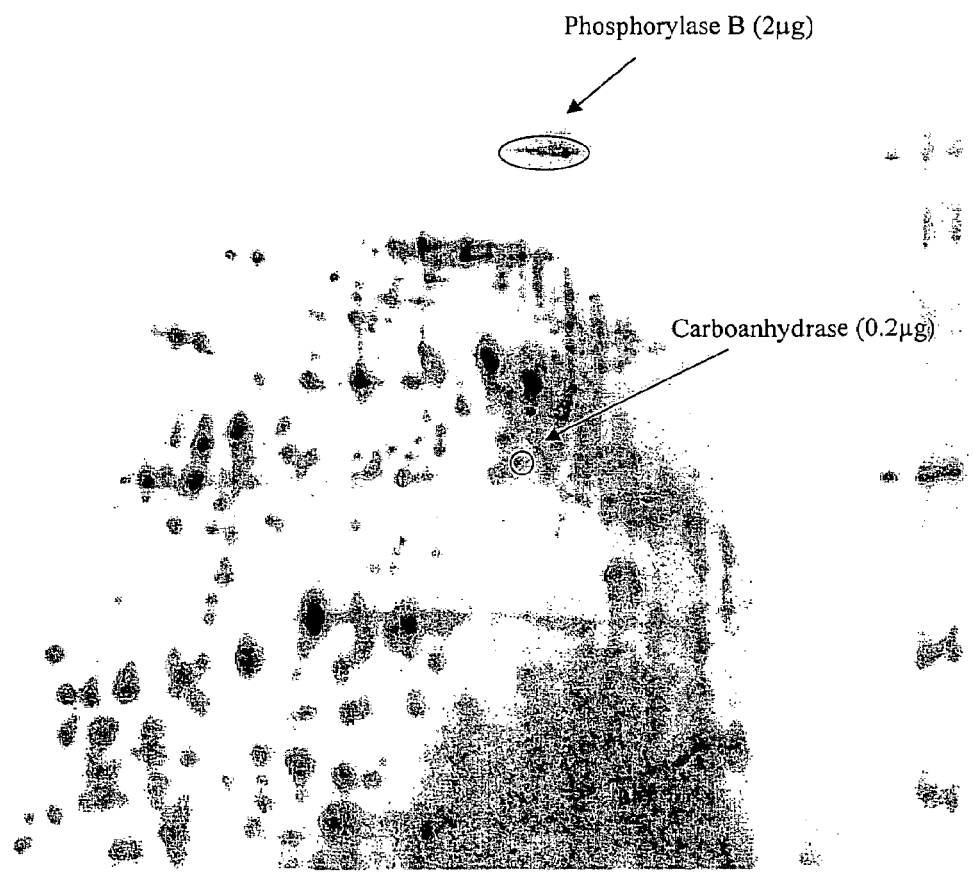

Furthermore, a typical 2D gel obtained with precipitated pancreatin with addition of two internal marker proteins Phosphorylase B and Carboanhydrase is shown in FIG. 7. Normalization, quantification, and the resulting matching process enables to compare the intensities of one spot referred to the intensities of the two internal marker proteins with a known amount of protein. In an example case according to the present invention phosphorylase B and carbonic anhydrase is spiked to all samples with a characteristic but always constant amount of protein (2 μg and 0.2 μg, respectively). It was shown that both proteins perform a constant pattern in the 2D-gel and do not overlap with existing spots of the pancreatic sample. Carbonic anhydrase only results in one single spot, phosphorylase B shows up in at least 5 isoforms, but both proteins can be spot-detected and therefore quantified very easily. A direct comparison of the intensities of a spot of interest with the intensities of the two marker proteins leads to an absolute quantification as soon as the intensity of the spot is within the range of the intensity of the marker proteins. To achieve statistically significant results all gels are run in replicates, at least three runs, and the groups of gels are compared with each other. The resulting average intensity of the spots is the basis for the comparison of the spots among each other.

Feasibility of RP-HPLC with MALDI-TOF-MS for Analysis of Pancreatin

Subject of the feasibility study is to show the usefulness of RP-HPLC with MALDI-TOF-MS for analysis of pancreatin, in particular precipitated pancreatin or pancreatin mini-microspheres. In the following tests the Peptidomics® platform (BioVisioN AG, Hannover) was applied for the characterization of precipitated pancreatin as outlined in detail below including detailed evaluation and validation with regard to specificity of the HPLC method As samples two batches of Pancreatin (batch 1 and batch 2) were used in the HPLC tests. The samples must be stored at 5+/−3° C., protected from light and humidity, e.g. in sealed bottles, until they are used for characterization. Before opening, the bottles should be adjusted to ambient conditions, e.g. by storing them at ambient conditions until equilibration is completed.

The HPLC method outlined below was used to examine the samples. Splitting into fractions with subsequent characterization by MALDI-TOF-MS was performed according to standard protocols known to the skilled artisan, e.g. protocols according to the Peptidomics® platform. The liquid chromatography is performed according to the European Pharmacopoeia (Ph. Eur., 2.2.29).

The protein and/or peptide pattern of characteristic constituents (compounds) of precipitated pancreatin is determined by gradient HPLC on a RP-18 reversed-phase column at the detection wavelength of 214 nm. Quantification is performed according to the Area % method. Generally, Ph. Eur. reagents are indicated by the letter R; quantities weighed or measured are commensurate with the degree of precision indicated in Ph. Eur. (1., General Notices). Furthermore, the term "water" without qualification means deionized water with a resistivity of NLT 0.18 MΩ m and a TOC of NMT 0.5 mg/ml. The following reagents were used in the test experiments:

Acetonitrile for chromatography R; e.g. Baker, no.: 9017
Trifluoroacetic acid R
Sodium chloride R
Solvent: Dissolution of 20.00 g of sodium chloride R in 1 l of water (2% NaCl solution)

The following instruments or equivalent systems also were used in the test experiments: Agilent HPLC-equipment consisting of:

AutosamplerG 1313A
ALSTherm G 1330A
Quat. pump G 1311A
UV-detector G 1314A
Vacuum degasser G 1322A
HP Column Oven G1316A
1100 control module G 1323A
LAN-interface 35900E
ChemServer Heraeus Biofuge 17RS or Equivalent System.

Column:
Type: MODULO O-CART QS UPTISPHERE 5 WRP, Interchim (UP5WRP$15QS)
Stationary phase: RP-18, 5.0 μm
Tubing material: stainless steel
Length: 150 mm
Internal diameter: 3.0 mm The HPLC tests are operated under the following conditions:

| Operating mode Mobile phase | Gradient HPLC | | |
|---|---|---|---|
| mobile phase A | water/TFA 0.05% (v/v) | | |
| mobile phase B | acetonitrile/TFA 0.05% (v/v) | | |
| Gradient | | | |
| Time [min] | % A | % B | |
| 0 | 100 | 0 | linear gradient to |
| 90 | 46 | 54 | linear gradient to |
| 90.1 | 100 | 0 | isocratic |
| 105 | 100 | 0 | equilibration |

Flow rate 1.0 ml/min
Period of analysis 95 min
Temperature 27 ± 2.0° C.
Injection volume 10 μl
Autosampler temperature 4° C. ± 1° C.

Detection was by a UV-detector at a wavelength of 214 nm.

Assay Preparation:

About 80.0 mg of the precipitated pancreatin to be examined are weighed in a 30 ml beaker. For examination of pancreatin enteric-coated mini-microspheres, the mini-microspheres must be grinded before and 140 mg of the powder are weighed in. The samples are to be dissolved in 10 ml of ice-cold Solvent while stirring at <4° C. for 15 minutes. Solutions are centrifuged (app. 8 ml; 10 min; 15000 U/min; 4° C.; For Heraeus Biofuge 17RS). The clear supernatant is to be injected as the sample solution. Sample Preparation has to be done freshly immediately before the sequence is started.

Performance:

Different batches of precipitated pancreatin and preparations thereof have already been examined by using the RP-HPLC method described above. The selectivity had been optimized to obtain the greatest number of peaks within a reasonable run-time. A typical chromatogram obtained with pancreatin batch 1 is depicted in the FIGS. 8 to 11 and Tables J and K.

Figure 8:
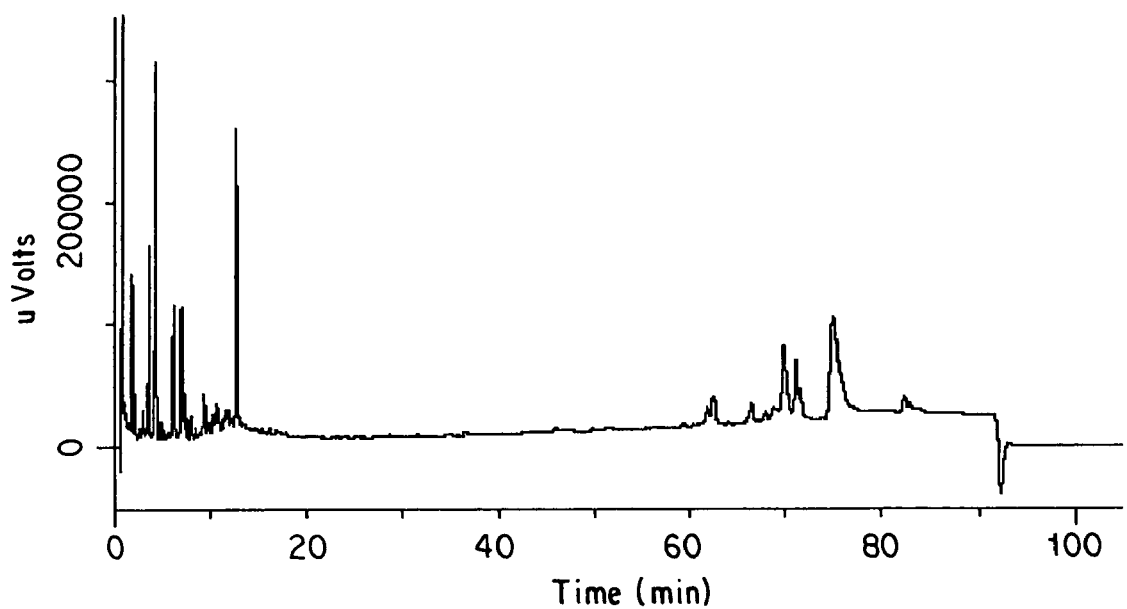
Figure 9:
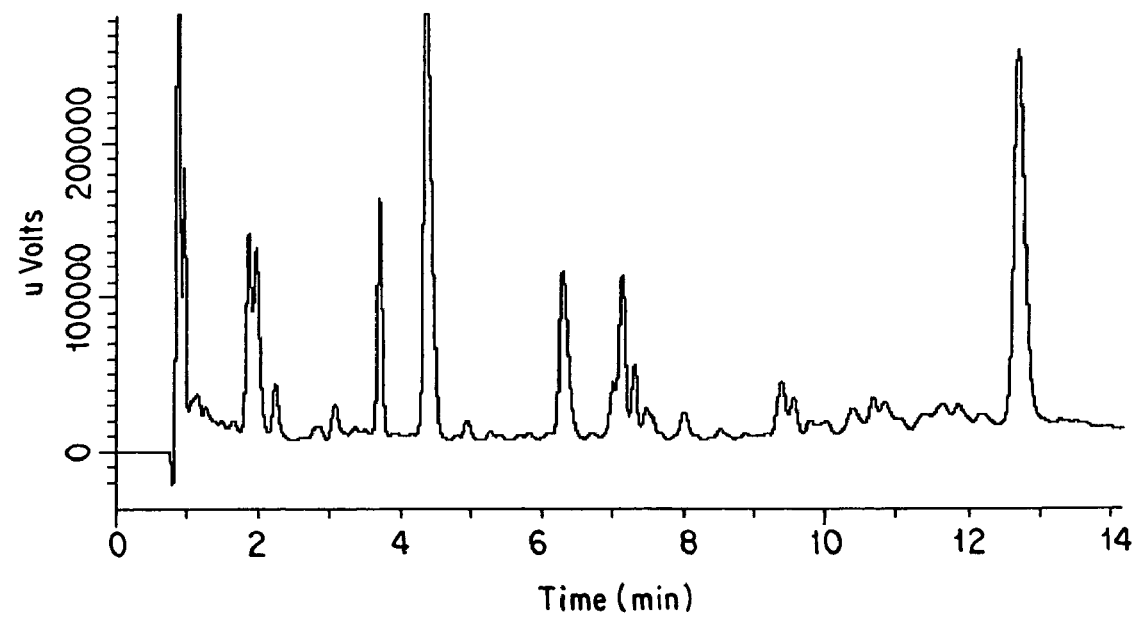
FIG. 9 Typical Chromatogram of Precipitated Pancreatin (0-14 min), Batch 1.
Figure 10:
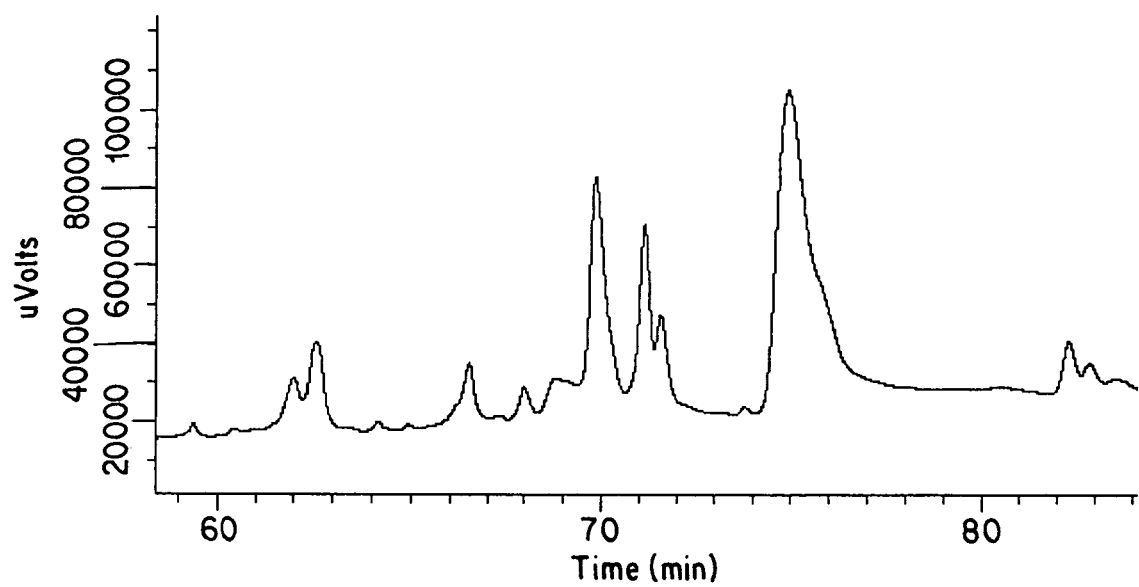
FIG. 10 Typical Chromatogram of Precipitated Pancreatin (60-90 min), Batch 1.
Figure 11:
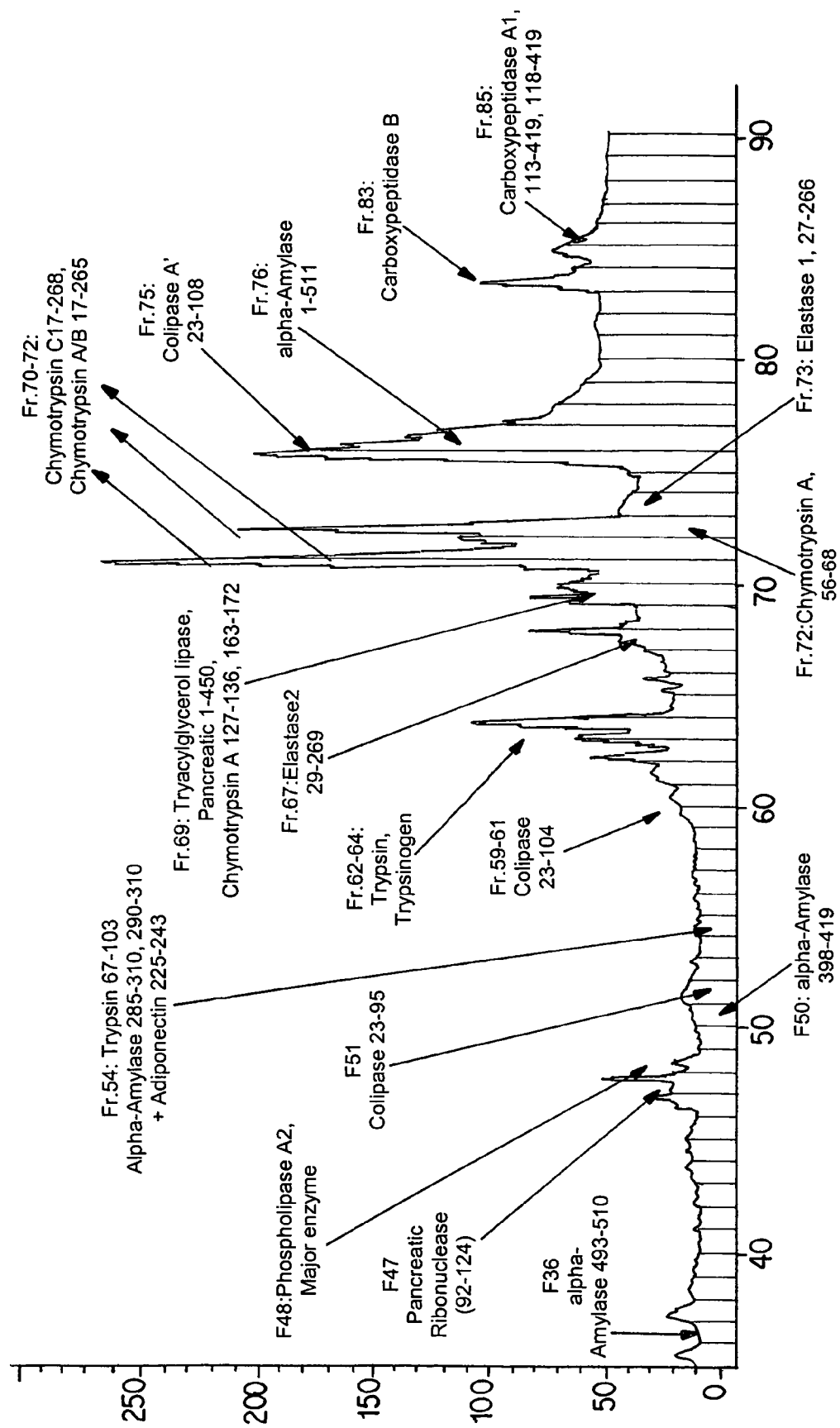
FIG. 11 Annotated RP-HPLC Chromatogram of Precipitated Pancreatin (min 35), Batch 1.

Contents of Tables J and K:
Table J Data for Spot Identification for Pancreatin (cf. FIG. 11): Identifications 20+
Table K Data for Spot Identification for Pancreatin (cf. FIG. 11): Identifications 20+X Contents of FIGS. 8 to 11:
FIG. 8 Typical Chromatogram of Precipitated Pancreatin, Batch 1
FIG. 9 Typical Chromatogram of Precipitated Pancreatin (0-14 min), Batch 1
FIG. 10 Typical Chromatogram of Precipitated Pancreatin (60-90 min), Batch 1
FIG. 11 Annotated RP-HPLC Chromatogram of Precipitated Pancreatin (min 35), Batch 1

With regard to evaluation of specificity and identification of peaks, coupling of LC to ESI-MS was already tried but signals were overlapping. Therefore, by applying the Peptidomics® technology, a sample of precipitated pancreatin was examined. The chromatogram was split automatically in 96 fractions, with one fraction corresponding to a run-time of approximately 55.1 seconds. Then, fractions were automatically pipetted together with the matrix of sinapinic acid on a target plate. Each single spot was subjected to MALDI-TOF-MS with multiple desorption and ionization after automatic positioning.

The mass range of interest to be considered covers m/z 1 to approximately 60,000. This range was visualized according to standard protocols for the Peptidomics® technology with quantification of single m/z signals. The m/z found were documented along with the corresponding fraction and the original chromatogram.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

TABLE A

Identified Spots from 2D-GE with Accession No. to NCBI Database: (cf. FIG. 1)

| Spot No.: | Protein Name | Accession N° | Mr/pI | Sequence coverage | Probability |
|---|---|---|---|---|---|
| 156 | alpha-amylase, pancreatic - pig | 67374 | 56.1/5.9 | 20% | 6.9e−11 |
| 644 | alpha-amylase [Sus scrofa] | 6056338 | 57.8/6.5 | 39% | 5.6e.43 |
| 813 | alpha-amylase [Sus scrofa] | 6056338 | 57.8/6.5 | 22% | 1.6e−04 |
| 1289 | procarboxypeptidase B [Sus scrofa] | 5457422 | 47.8/5.2 | 60% | 4.4e−46 |
| 1455 | carboxypeptidase A1 precursor [Sus scrofa] | 4336169 | 47.3/5.1 | 32% | 1.0e−11 |
| 1761 | pig alpha-amylase | 1942950 | 55.9/6.2 | 20% | 2.9e−08 |
| 4132 | androgen receptor [Sus scrofa] | 11559518 | 97.1/6.0 | 8% | MS Fit |
| 5883 | trypsin precursor - pig | 136429 | 25.1/7.1 | 54% | 1e−03 |
| 5993 | trypsin-precursor - pig | 136429 | 25.1/7.1 | 71% | 4.3e−14 |
| 1207 | phospholipase A2 (phosphatidylcholine 2-acylhydrolase) - pig | 129436 | 14.8/5.6 | 41% | 3.8e−08 |
| 12359 | Chain B, porcine E-Trypsin | 999627 | 8.8/6.7 | | |
| 1246 | alpha-amylase [Scus scrofa] | 6056338 | 57.8/6.5 | | |
| 126 | alpha-amylase - pig | 1942950 | 55.9/6.2 | | |
| 1261 | oviduct-specific glycoprotein precursor [Sus scrofa] | 2493679 | 58.8/9.2 | | |
| 12998 | triacylglycerol lipase - pig | 67161 | 50.6/5.6 | | |
| 131-1 | triacylglycerol lipase - pig | 67161 | 50.7/5.6 | 41% | 2.0e−18 |
| 13190 | alpha-amylase [scus scrofa] | 6056338 | 57.8/6.5 | 38% | 1.4e−28 |
| 1381 | alpha-amylase, pancreatic - pig | 67374 | 56.1/5.9 | 24% | 8.8e−05 |
| 1710 | procarboxypeptidase B [Sus scrofa] | 5457422 | 47.8/5.2 | 50% | 4.4e−27 |
| 1743 | alpha-amylase [Sus scrofa] | 6056338 | 57.8/6.5 | 27% | 5.4e−14 |
| 1767-1 | phosphodiesterase 6B [Mus musculus] | 6679255 | 99.6/5.3 | 12% | 6.3e−05 |
| 1767-2 | elastase, pancreatic - human | 88301 | 30.0/6.4 | | |
| 1817 | steroid membrane binding protein | 47522662 | 21.6/4.6 | 13% | MS Fit |
| 1914 | triacylglycerol lipase, pancreatic (pancreatic lipase) - pig | 6686288 | 50.9/5.7 | 62% | 1.6e−31 |
| 1974 | alpha-amylase [Sus scrofa] | 6056338 | 57.8/6.5 | 18% | 1.3e−03 |
| 2033 | type III cytochrome P450 aromatase [Sus scrofa] | 1762231 | 47.5/8.8 | 22% | 7.0e−03 |
| 2046 | chymotrypsin-like proteinase - pig | 89257 | 13.4/4.6 | | |
| 2066-1 | transforming growth factor neta 1 [Sus scrofa] | 89305 | 44.3/8.9 | | |
| 2066-2 | elastase isoform 2, pancreatic - human | 7435612 | | | |
| 2068 | pig alpha-amylase | 1942950 | 56.0/6.0 | | |
| 223 | ladinin 1 (Lad-1) | 12643530 | 57.2/9.7 | 14% | 9.2e−07 |
| 2322 | envelope glycoprotein [Sus scrofa] | 37545606 | 24.3/8.7 | 18% | MS Fit |
| 2380 | pig alpha-amylase | 1942950 | 55.9/6.2 | 21% | 8.5e−05 |
| 2420 | elastase 1, pancreatic - pig | 355937 | 29.3/9.1 | 35% | 4.6e−05 |
| 2524-1 | glucose-6-phosphat isomerase [Sus scrofa] | 47523720 | 63.1/7.9 | 14% | MS Fit |
| 2524-2 | N-acetyl-beta-D-glucosaminide alpha-1,6-fucosyltransferase [Sus scrofa] | 47522688 | 66.2/7.4 | 6% | MS Fit |
| 2622 | phospholipase A2 - pig | 129436 | 14.8/5.6 | 41% | 3.9e−06 |
| 2679 | alpha-amylase [Sus scrofa] | 6056338 | 57.8/6.5 | 27% | 1.9e−24 |
| 2712 | pancreatic colipase - pig | 1082974 | 10.9/5.6 | 62% | 1.8e−07 |
| 278 | trypsin [Sus scrofa] | 136429 | 25.1/7.0 | | |
| 2783 | elastase 2, precursor - pig | 47523026 | 28.7/8.3 | 34% | MS Fit |
| 3316 | alpha-1-antychymotrypsin [Sus scrofa] | 9968807 | 22.9/5.8 | 31% | 7.1e−13 |
| 4105 | triacylglycerol lipase, pancreatic - pig | 6686288 | 50.1/5.7 | 11% | MS Fit |
| 4318 | cytochrome P-450 11A1 [Sus scrofa] | 47523912 | 60.3/9.1 | 11% | MS Fit |
| 4488 | alpha amylase [sus scrofa] | 6056338 | 57.8/6.5 | 16% | 1.9e−07 |
| 4488 | alpha amylase [sus scrofa] | 6056338 | 57.8/6.5 | 16% | 1.9e−07 |
| 4780 | 17a-hydroxylase cytochrome P450 | 833797 | 56.4/8.9 | 5% | MS Fit |
| 4790 | cytochrome P-450-j [Sus scrofa] | 47523896 | 57.1/8.1 | 13% | MS Fit |
| 5027 | Chain C, Porcine E-Trypsin | 999628 | 10.5/8.7 | | |
| 7 | alpha-amylase, pancreatic (1,4-alpha-D-glucan glucanhydrolase) - pig | 2811088 | 56.0/5.8 | 28% | 5.1e−23 |
| 931 | alpha-amylase pancreatic - pig | 67374 | 56.1/5.9 | 40% | 3.7e−52 |

TABLE B

Spot intensities for Pancreatin Batch 1 (t = 0 and 16 days) with average and standard deviation and regulation of spot vs. t0

| | | t0 | | | | 16 days | | | | | |
|---|---|---|---|---|---|---|---|---|---|---|---|
| Degradation[1] | Spot ID | I.1.1 | I.1.2 | Average | Sdv. [%] | I.2.1 | I.2.2 | I.2.3 | Regulation Ref t0 | Average | sdv. [%] |
| 0 | 1207 | 4078.048 | 3792.744 | 3932.81 | 3.69 | 3650.85 | 4045.124 | 4337.619 | 1.02 | 4001.219 | 7.34 |
| − | 12359 | 8021.147 | 6576.846 | 7263.184 | 10.44 | 4696.391 | 4601.163 | 4965.734 | 0.65 | 4751.949 | 3.27 |
| − | 1246 | 9159.915 | 8065.862 | 8595.5 | 6.57 | 215.146 | 162.368 | 356.896 | 0.03 | 231.878 | 38.52 |
| + | 126 | 4229.222 | 4035.89 | 4131.425 | 2.37 | 6660.025 | 7209.74 | 7165.684 | 1.70 | 7007.306 | 3.67 |
| − | 1261 | 4949.297 | 5896.791 | 5402.312 | 9.15 | 5164.268 | 5806.186 | 3198.433 | 0.85 | 4577.331 | 29.43 |
| − | 1289 | 9260.927 | 12851.92 | 10909.661 | 17.80 | 11221.78 | 9950.6 | 10055.62 | 0.95 | 10393.772 | 5.59 |
| 0 | 12998 | 1868.685 | 2344.636 | 2093.177 | 12.01 | 2248.892 | 2524.705 | 2731.853 | 1.19 | 2493.899 | 8.32 |
| − | 131 | 4011.788 | 7697.141 | 5556.915 | 38.51 | 4862.033 | 5331.125 | 4533.823 | 0.88 | 4898.169 | 6.86 |

TABLE B-continued

Spot intensities for Pancreatin Batch 1 (t = 0 and 16 days) with average and standard deviation and regulation of spot vs. t0

| Degradation[1] | Spot ID | t0 | | | | 16 days | | | | | |
|---|---|---|---|---|---|---|---|---|---|---|---|
| | | I.1.1 | I.1.2 | Average | Sdv. [%] | I.2.1 | I.2.2 | I.2.3 | Regulation Ref t0 | Average | sdv. [%] |
| − | 1381 | 1771.956 | 1990.661 | 1878.128 | 5.99 | 323.27 | 351.962 | 455.117 | 0.20 | 372.73 | 15.65 |
| − | 1455 | 10298.58 | 13972.09 | 11995.528 | 16.48 | 14085.23 | 15643.25 | 14747.8 | 1.23 | 14811.739 | 4.39 |
| + | 156 | 3298.121 | 5527.63 | 4269.753 | 29.46 | 3220.649 | 7817.308 | 6538.588 | 1.28 | 5480.601 | 46.66 |
| 0 | 1767 | 7616.371 | 7807.967 | 7711.574 | 1.25 | 8839.614 | 9898.697 | 10648.86 | 1.27 | 9767.23 | 7.96 |
| − | 1817 | 9981.82 | 8936.962 | 9444.953 | 5.68 | 4809.418 | 4414.818 | 4460.521 | 0.48 | 4558.238 | 3.89 |
| − | 1914 | 937.731 | 1112.352 | 1021.316 | 8.91 | 303.047 | 414.163 | 428.131 | 0.37 | 377.357 | 16.84 |
| − | 1974 | 4748.027 | 4694.271 | 4721.072 | 0.57 | 2172.757 | 2239.186 | 2356.783 | 0.48 | 2254.968 | 3.41 |
| + | 2033 | 990.63 | 963.999 | 977.224 | 1.37 | 2609.319 | 2329.106 | 1884.798 | 2.31 | 2254.207 | 14.43 |
| − | 2046 | 5848.565 | 5616.127 | 5731.168 | 2.05 | 2736.17 | 2725.604 | 2949.172 | 0.49 | 2801.788 | 3.70 |
| − | 2066 | 5586.802 | 7924.223 | 6653.65 | 19.10 | 4131.944 | 7178.561 | 7058.878 | 0.89 | 5938.031 | 29.24 |
| − | 2068 | 5113.109 | 4722.385 | 4913.865 | 4.05 | 2062.239 | 2733.004 | 2877.695 | 0.52 | 2531.287 | 15.77 |

[1] 0 = no change during study, + = increase, − = decrease of intensity

TABLE C

Spot intensities for Pancreatin Batch 1 (t = 0 and 16 days) with average and standard deviation and regulation of spot vs. t0

| Degradation[2] | Spot ID | t0 | | | | 16 days | | | | | |
|---|---|---|---|---|---|---|---|---|---|---|---|
| | | I.1.1 | I.1.2 | Average | Sdv. [%] | I.2.1 | I.2.2 | I.2.3 | Regulation Ref t0 | Average | sdv. [%] |
| − | 223 | 2875.863 | 2644.019 | 2757.505 | 4.29 | N.A. | N.A. | N.A. | 0.00 | N.A. | N.A. |
| − | 2380 | 957.904 | 1614.924 | 1243.761 | 29.84 | 1330.991 | 1187.463 | N.A. | 1.01 | 1257.18 | 5.87 |
| − | 2524 | 1158.452 | 1236.086 | 1196.639 | 3.30 | 1285.804 | 1222.937 | 1368.273 | 1.08 | 1290.973 | 4.70 |
| − | 2679 | 1376.759 | 1477.267 | 1426.128 | 3.59 | 867.595 | 754.456 | 945.068 | 0.60 | 852.062 | 9.73 |
| 0 | 2712 | 8153.147 | 7120.373 | 7619.281 | 7.01 | 8498.175 | 9118.323 | 9275.288 | 1.18 | 8957.553 | 3.86 |
| − | 4105 | 2719.599 | 2687.769 | 2703.637 | 0.59 | 2014.855 | 1172.338 | 1170.661 | 0.52 | 1403.598 | 29.13 |
| − | 4132 | 1696.162 | 1862.568 | 1777.419 | 4.79 | N.A. | N.A. | N.A. | 0.00 | N.A. | N.A. |
| − | 4488 | 3712.759 | 3650.984 | 3681.742 | 0.84 | 1590.102 | 1855.598 | 2122.936 | 0.50 | 1843.381 | 12.53 |
| − | 4780 | 2867.793 | 2769.423 | 2818.179 | 1.76 | N.A. | N.A. | N.A. | 0.00 | N.A. | N.A. |
| − | 4790 | 1275.707 | 1454.507 | 1362.177 | 6.78 | N.A. | N.A. | N.A. | 0.00 | N.A. | N.A. |
| − | 7 | 2530.903 | 2616.458 | 2573.325 | 1.68 | 926.152 | 1065.491 | 1093.86 | 0.40 | 1025.805 | 7.58 |

[2] 0 = no change during study, + = increase, − = decrease of intensity

TABLE D

Spot intensities for Pancreatin Batch 1 (t = 32 days) with average and standard deviation and regulation of spot vs. t0

| Degradation[3] | Spot | I.3.1 | I.3.2 | I.3.3 | Regulation Ref t0 | Average | sdv [%] |
|---|---|---|---|---|---|---|---|
| 0 | 1207 | 3979.887 | 3986.699 | 3718.964 | 0.99 | 3893.158 | 3.29 |
| − | 12359 | 5479.002 | 5931.415 | 3106.072 | 0.64 | 4656.116 | 33.39 |
| − | 1246 | 227.847 | 424.84 | 388.771 | 0.04 | 335.11 | 31.68 |
| + | 126 | 9162.12 | 8602.472 | 7805.051 | 2.06 | 8504.817 | 6.82 |
| − | 1261 | 6256.069 | 3729.149 | 3971.882 | 0.84 | 4525.18 | 25.92 |
| − | 1289 | 10337.988 | 9444.828 | 10833.402 | 0.93 | 10189.002 | 5.86 |
| 0 | 12998 | 1991.713 | 2320.616 | 2046.659 | 1.01 | 2114.909 | 6.88 |
| − | 131 | 4112.75 | 4149.592 | 4294.907 | 0.75 | 4185.016 | 1.89 |
| − | 1381 | N.A. | N.A. | N.A. | 0.00 | N.A. | N.A. |
| − | 1455 | 15705.897 | 12436.6 | 13143.237 | 1.14 | 13692.694 | 10.47 |
| + | 156 | 6908.462 | 7318.195 | 5965.959 | 1.57 | 6706.386 | 8.98 |
| 0 | 1767 | 8853.396 | 7161.024 | 10372.317 | 1.13 | 8696.015 | 16.39 |
| − | 1817 | 5639.384 | 5499.357 | 6142.168 | 0.61 | 5753.805 | 4.84 |
| − | 1914 | 466.887 | 492.839 | 261.301 | 0.38 | 391.759 | 33.27 |
| − | 1974 | 959.261 | 947.507 | 1110.288 | 0.21 | 1003.04 | 7.47 |
| + | 2033 | 2014.629 | 1459.351 | 2233.122 | 1.92 | 1872.502 | 19.87 |
| − | 2046 | 3574.896 | 3794.235 | 2834.71 | 0.59 | 3375.195 | 13.40 |
| − | 2066 | 5628.97 | 4877.957 | 3242.119 | 0.67 | 4465.107 | 26.33 |
| − | 2068 | 958.091 | 1250.93 | 909.724 | 0.21 | 1029.24 | 14.98 |

[3] 0 = no change during study, + = increase, − = decrease of intensity

TABLE E

Spot intensities for Pancreatin Batch 1 (t = 32 days) with average and standard deviation and regulation of spot vs. t0

| Degradation[4] | Spot | I.3.1 | I.3.2 | I.3.3 | Regulation Ref t0 | Average | sdv [%] |
|---|---|---|---|---|---|---|---|
| − | 223 | N.A. | N.A. | N.A. | 0.00 | N.A. | N.A. |
| − | 2380 | N.A. | N.A. | N.A. | 0.00 | N.A. | N.A. |
| − | 2524 | 684.712 | 649.971 | 721.914 | 0.57 | 684.903 | 4.38 |
| − | 2679 | N.A. | N.A. | N.A. | 0.00 | N.A. | N.A. |
| 0 | 2712 | 8735.452 | 6751.801 | 7378.296 | 0.99 | 7577.984 | 11.28 |
| − | 4105 | 1273.323 | N.A. | N.A. | 0.47 | 1273.323 | N.A. |
| − | 4132 | N.A. | N.A. | N.A. | 0.00 | N.A. | N.A. |
| − | 4488 | 792.199 | 828.132 | 1044.736 | 0.24 | 881.685 | 12.90 |
| − | 4780 | N.A. | N.A. | N.A. | 0.00 | N.A. | N.A. |
| − | 4790 | N.A. | N.A. | N.A. | 0.00 | N.A. | N.A. |
| − | 7 | 645.021 | 555.266 | 550.648 | 0.23 | 582.08 | 7.54 |

[4]0 = no change during study, + = increase, − = decrease of intensity

TABLE F

Spot intensities for Pancreatin Batch 2 (t = 0 and 15 days) with average and standard deviation and regulation of spot vs. t0

| D[5] | Spot ID | I.1.1 | I.1.2 | I.1.3. | Average | Sdv. [%] | I.2.1 | I.2.2 | I.2.3 | Regul.- Ref t0 | Average | sdv. [%] |
|---|---|---|---|---|---|---|---|---|---|---|---|---|
| 0 | 1207 | 70410.727 | 70104.594 | 78435.242 | 72884 | 5.33 | 59955.207 | 62538.777 | 77464.266 | 0.91 | 66225.602 | 11.87 |
| − | 12359 | 213088.703 | 147347 | 175938.297 | 176774.938 | 16.26 | 187573.031 | 197302.594 | 190839.766 | 1.09 | 191862.766 | 2.12 |
| − | 1246 | 97149.695 | 104896.492 | 101615.938 | 101170.695 | 3.20 | 121943.484 | 136823.172 | 169640.141 | 1.40 | 141454.125 | 14.66 |
| + | 126 | 151115.266 | 158836.781 | 142001.266 | 150493.313 | 4.69 | 191755.484 | 185599.875 | 212478.844 | 1.30 | 196281.969 | 5.93 |
| − | 1261 | 106723.523 | 105456.211 | 130820.516 | 113763.445 | 10.40 | 95200.484 | 93413.656 | 119793.773 | 0.90 | 102131.867 | 11.97 |
| − | 1289 | 190093.344 | 139408.188 | N.A. | 162789.953 | 16.77 | 151575.344 | 161213.063 | 173787.297 | 0.99 | 161938.063 | 5.75 |
| − | 12998 | 38122.777 | 35706.887 | 32991.051 | 35544.922 | 6.09 | 25088.756 | 23895.512 | 21836.1 | 0.66 | 23568.043 | 5.92 |
| 0 | 131 | 88975.648 | 111207.109 | 75701.594 | 90817.508 | 17.08 | 68287.352 | 68784.063 | 96764.992 | 0.85 | 76886.266 | 17.66 |
| − | 1381 | 12974.204 | 12174.2 | 15987.4 | 13617.571 | 12.34 | 9131.455 | 9652.959 | 11400.876 | 0.74 | 10016.429 | 9.89 |
| − | 1455 | 314480.219 | 289503.844 | 188071.266 | 257744.875 | 25.28 | 255962.609 | 274785.219 | 386938.656 | 1.17 | 300795.031 | 19.77 |
| − | 1761 | 15691.019 | 20691.357 | 13563.425 | 16390.914 | 19.14 | 13345.886 | 11320.138 | 8699.047 | 0.67 | 10953.602 | 19.28 |
| − | 1767 | 212890.234 | 154120.344 | 111851.688 | 154247.953 | 30.05 | 144958.578 | 159549.328 | 129887.758 | 0.94 | 144289.828 | 8.77 |
| − | 1817 | 186074.484 | 199486.219 | 211798.969 | 198841.875 | 5.43 | 219332.703 | 204378.953 | 218279.266 | 1.08 | 213886.813 | 3.27 |
| − | 1914 | 8234.748 | 11394.64 | 7151.643 | 8754.921 | 21.54 | 7055.372 | 7289.475 | 6135.638 | 0.78 | 6808.09 | 7.76 |
| − | 1974 | 57885.094 | 50931.77 | 58662.637 | 55715.027 | 6.58 | 37022.191 | 37422.117 | 36630.828 | 0.66 | 37023.637 | 0.88 |
| ? | 2033 | 19155.631 | 31398.879 | 22173.328 | 23714.492 | 23.03 | 18588.197 | 12040.256 | 12272.449 | 0.59 | 14004.516 | 22.19 |
| − | 2046 | 141966.344 | 110510.75 | 71840.992 | 104068.852 | 32.48 | 157937.969 | 139401.516 | 124661.922 | 1.35 | 140011.156 | 10.15 |
| − | 2066 | 166670.281 | 223431.359 | 134839.516 | 171240.5 | 23.01 | 95422.578 | 95208.539 | 97034.086 | 0.56 | 95884.953 | 0.85 |
| − | 2068 | 41946.742 | 50023.508 | 43994.121 | 45194.855 | 7.72 | 19809.289 | 23673.643 | 22384.219 | 0.48 | 21895.689 | 7.72 |

[5]Degradation: 0 = no change during study, + = increase, − = decrease of intensity

TABLE G

Spot intensities for Pancreatin Batch 2 (t = 0 and 15 days) with average and standard deviation and regulation of spot vs. t0

| D[6] | Spot ID | I.1.1 | I.1.2 | Average | Sdv. [%] | I.2.1 | I.2.2 | I.2.3 | Regul. Ref t0 | Average | sdv. [%] |
|---|---|---|---|---|---|---|---|---|---|---|---|
| − | 223 | 70134.547 | 71777.023 | 68743.836 | 70207.539 | 1.78 | 101422.148 | 99083.82 | 101165.242 | 1.43 | 100551.594 | 1.05 |
| − | 2380 | 20123.006 | 20353.197 | 29129.984 | 22850.125 | 18.74 | 31887.355 | 24744.543 | 15810.367 | 1.02 | 23192.449 | 33.65 |
| − | 2524 | 14514.978 | 14838.783 | 15556.002 | 14963.65 | 2.93 | 8014.343 | 8482.458 | 7274.182 | 0.53 | 7907.841 | 6.55 |
| 0 | 2622 | 88859.688 | 95788.625 | 109042.695 | 97545.016 | 8.82 | 72266.852 | 79633.148 | 100843.906 | 0.86 | 83411.813 | 15.02 |
| − | 2679 | 21288.855 | 20359.092 | 17436.951 | 19624.281 | 8.93 | 9086.135 | 10192.972 | 11742.738 | 0.52 | 10283.709 | 11.06 |
| 0 | 2712 | 154324.953 | 171617.516 | 153426.281 | 159575.359 | 5.28 | 123272.273 | 131906.547 | 128145.391 | 0.80 | 127725.688 | 2.81 |
| − | 4132 | 17919.049 | 18716.396 | 21376.762 | 19282.338 | 7.79 | 21209.465 | 21223.914 | 17571.139 | 1.03 | 19924.391 | 9.29 |
| − | 4488 | 35711.895 | 36804.625 | 39441.484 | 37286.891 | 4.25 | 19991.75 | 20630.113 | 19977.719 | 0.54 | 20197.584 | 1.51 |
| − | 4780 | 26554.484 | 32128.514 | 14705.147 | 23236.246 | 39.48 | 26276.857 | 28980.635 | 22816.873 | 1.11 | 25900.758 | 10.31 |

TABLE G-continued

Spot intensities for Pancreatin Batch 2 (t = 0 and 15 days) with average and standard deviation and regulation of spot vs. t0

| | | t0 | | | | 15 days | | | | | |
|---|---|---|---|---|---|---|---|---|---|---|---|
| D[6] | Spot ID | I.1.1 | I.1.2 | Average | Sdv. [%] | I.2.1 | I.2.2 | I.2.3 | Regul. Ref t0 | Average | sdv. [%] |
| – | 4790 | 10532.181 | 11177.513 | 7676.267 | 9668.026 | 17.93 | 9546.312 | 11794.334 | 8648.206 | 1.03 | 9911.629 | 13.82 |
| – | 7 | 20862.508 | 20863.723 | 18351.205 | 19989.762 | 6.23 | 12104.132 | 11661.612 | 11381.058 | 0.59 | 11711.835 | 2.57 |

[6]Degradation: 0 = no change during study, + = increase, – = decrease of intensity

TABLE H

Spot intensities for Pancreatin Batch 2 (t = 32 days) with average and standard deviation and regulation of spot vs. t0

| | | 32 days | | | | | |
|---|---|---|---|---|---|---|---|
| Degradation[7] | Spot | I.3.1 | I.3.2 | I.3.3 | Regulation Ref t0 | Average | sdv [%] |
| 0 | 1207 | 90339.25 | 82992.906 | 90244.383 | 1.20 | 87790.164 | 4.05 |
| – | 12359 | 113074.078 | 155135.547 | 118655.805 | 0.72 | 127679.484 | 14.93 |
| – | 1246 | 44936.344 | 36451.109 | 39889.012 | 0.40 | 40276.703 | 8.95 |
| + | 126 | 209982.422 | 165129.609 | 213440.969 | 1.29 | 194877.594 | 12.45 |
| – | 1261 | 123483.938 | 89137.664 | 90827.406 | 0.88 | 99991.453 | 16.12 |
| – | 1289 | 156977.578 | 102686.602 | 99013.484 | 0.72 | 116864.313 | 23.27 |
| – | 12998 | 18334.098 | 18471.773 | 13933.649 | 0.47 | 16773.01 | 14.02 |
| 0 | 131 | 105044.617 | 90399.398 | 98988.914 | 1.08 | 97958.461 | 6.37 |
| – | 1381 | 3661.021 | N.A. | N.A. | 0.00 | N.A. | N.A. |
| – | 1455 | 225169.469 | 190251.938 | 170228.453 | 0.75 | 193920.438 | 12.19 |
| – | 1761 | 5739.493 | N.A. | N.A. | 0.00 | N.A. | N.A. |
| – | 1767 | 75451.969 | 131763.344 | N.A. | 0.65 | 99708.594 | 32.15 |
| – | 1817 | 197082.078 | 134650.938 | 170172.078 | 0.83 | 165290.641 | 16.98 |
| – | 1914 | 5876.411 | 5032.68 | N.A. | 0.62 | 5438.207 | 8.06 |
| – | 1974 | 7621.188 | 6571.003 | 5024.076 | 0.11 | 6313.015 | 18.82 |
| ? | 2033 | 31489.441 | 17034.555 | 31166.553 | 1.08 | 25569.85 | 33.27 |
| – | 2046 | 69711.344 | 130779.367 | 41067.059 | 0.51 | 53505.512 | 30.29 |
| – | 2066 | 73859.352 | 109141.953 | 71584.461 | 0.49 | 83254.039 | 21.15 |
| – | 2068 | 19679.99 | 13170.204 | 23304.211 | 0.40 | 18211.705 | 27.04 |

[7]0 = no change during study, + = increase, – = decrease of intensity

TABLE I

Spot intensities for Pancreatin Batch 2 (t = 32 days) with average and standard deviation and regulation of spot vs. t0

| | | 32 days | | | | | |
|---|---|---|---|---|---|---|---|
| Degradation[8] | Spot | I.3.1 | I.3.2 | I.3.3 | Regulation Ref t0 | Average | sdv [%] |
| – | 223 | 19150.346 | 16766.926 | 17665.701 | 0.25 | 17834.201 | 5.62 |
| – | 2380 | N.A. | N.A. | N.A. | 0.00 | N.A. | N.A. |
| – | 2524 | 4161.9 | 5392.458 | 5381.154 | 0.33 | 4942.932 | 12.93 |
| 0 | 2622 | 94891.992 | 97860.477 | 93523.508 | 0.98 | 95408.242 | 1.91 |
| – | 2679 | N.A. | N.A. | N.A. | 0.00 | N.A. | N.A. |
| 0 | 2712 | 153619 | N.A. | 153772.938 | 0.96 | 153695.953 | 0.05 |
| – | 4132 | 9918.519 | 6933.719 | 5683.137 | 0.38 | 7311.397 | 25.91 |
| – | 4488 | 7064.731 | 5263.715 | 5626.913 | 0.16 | 5936.804 | 13.43 |
| – | 4780 | 6016.258 | 10940.175 | N.A. | 0.35 | 8112.886 | 34.85 |
| – | 4790 | N.A. | N.A. | N.A. | 0.00 | N.A. | N.A. |
| – | 7 | 6380.595 | 2987.297 | 4538.519 | 0.22 | 4422.67 | 36.39 |

[8]0 = no change during study, + = increase, – = decrease of intensity

TABLE J

Data for Spot Identification for Pancreatin (cf. FIG. 11): Identifications 20+

| Fraction | Protein | Acc. No. (SwissProt) | Position | Mr (exp., kDa) |
|---|---|---|---|---|
| 17 | Trypsin activation peptide | P00761 | 1-8 | 0.95 kDa |
| 36 | alpha-Amylase | P00690 | 493-510 | 1.9 kDa |

TABLE J-continued

Data for Spot Identification for Pancreatin (cf. FIG. 11): Identifications 20+

| Fraction | Protein | Acc. No. (SwissProt) | Postion | Mr (exp., kDa) |
|---|---|---|---|---|
| 47 | Pancreatic Ribonuclease component | P00671 | 92-124 | low abundant |
| 48 | Phospholipase A2, major enzyme | P00592 | 23-146 (complete) | 13.98 kDa |
| 51 | alpha-Amylase | P00690 | 293-310, 422-444 | 2.10 kDa; 2.6 kDa |
| 52 | Colipase | P02703 | 23-95 | 7.9 kDa |
| 54 | Trypsin | P00761 | 67-103 | 4.04 Da |
| 54 | alpha-Amylase | P00690 | 290-310, 285-310 | 2.46 kDa; 2.95 kDa |
| 54 | Adiponectin | Q7YRF8 (TrEMBL) | 225-243 | 2.18 kDa |
| 55 | Trypsin | P00761 | 67-102 | 3.94 kDa |
| 59-61 | Colipase | P02703 | 23-104 | 9.03 kDa |

TABLE K

Data for Spot Identification for Pancreatin (cf. FIG. 11): Identifications 20 + X

| Fraction | Protein | Acc. No. (SwissProt) | Postion | Mr (exp., kDa) |
|---|---|---|---|---|
| 62-64 | Trypsinogen | P00761 | 1-231 (complete) | 24.4 kDa |
| 62-64 | Trypsin | P00761 | 9-231 (complete) | 23.5 kDa |
| 67 | Elastase 2 | P08419 | 29-269 (complete) | 25.8 kDa |
| 69 | Triacylglycerol lipase | P00591 | 1-450 (complete) | 50.1 kDa |
| 69 | Chymotrypsin A/B | Q9ER05 (MSD8 mouse) | 127-136, 163-373 | 26.0-27.5 kDa |
| 70-71 | Chymotrypsin C | Q99895 (human) | 57-268, 17-268 | 26.0-27.5 kDa |
| 70-71 | Chymotrypsin A/B | Q9ER05 (MSD8 mouse) | 163-173 | 26.0-27.5 kDa |
| 72 | Chymotrypsin A/B | Q9ER05 (MSD8 mouse) | 56-68 | 26.0-27.5 kDa |
| 73 | Elastase 1 | P00772 | 27-266 (complete) | 25.90 kDa |
| 75 | Colipase A' | P02703 | 23-108 (complete) | 9.28 kDa |
| 76-78 | alpha-Amylase | P00690 | 17-511 (complete) | 55.4 kDa |
| 83 | Carboxypeptidase B | P09955 | 96-401 (complete) | 34.5 kDa |
| 85 | Carboxypeptidase A1 | P09954 | 113-419, 118-419 | 34.4 kDa, 33.9 kDa |

What is claimed is:

1. A method for analyzing a protein sample containing a physiologically-acceptable digestive enzyme mixture with lipolytic, proteolytic and amylolytic activity by two-dimensional gel electrophoresis, wherein the mixture can be used in the manufacture of a pharmaceutical preparation, said method comprising:
   (a) preparing the protein sample by dissolving the sample in a gel electrophoresis solvent composition comprising a protein solving solvent, an internal standard for quantifying proteins, and a protease inhibitor;
   (b) defining the first dimension of the gel electrophoresis by isoelectric focusing, and applying a gradient to separate protein fractions;
   (c) re-buffering the protein fractions;
   (d) transferring the protein fractions from (c) to the second dimension of the gel electrophoresis and separating components of the fractions by SDS-PAGE;
   (e) fixing and staining SDS-PAGE gels resulting from (d);
   (f) evaluating the gels densitometrically by fluorescence scanning; and
   (g) determining the identity and absolute quantity of one or more proteins in the digestive enzyme mixture.

2. A method according to claim 1, wherein said enzyme mixture is a mixture of microbially synthesized lipases, proteases and amylases.

3. A method according to claim 1, wherein said enzyme mixture is a mixture of digestive enzymes from a mammal.

4. A method according to claim 1, wherein said enzyme mixture comprises pancreatin.

5. A method according to claim 4, wherein said pancreatin is precipitated pancreatin.

6. A method according to claim 4, wherein said pancreatin is in the form of pancreatin mini-microspheres.

7. A method according to claim 1, wherein the solvent used in (a) to dissolve the sample is a lysis buffer comprising 7M urea, 2M thiourea, 4% (w/v) CHAPS, 1% (w/v) DTT, and 0.5% PHARMALYTE at pH 3-10.

8. A method according to claim 1, wherein the internal standard for quantifying proteins is phosphorylase B or carbonic anhydrase.

9. A method according to claim 8, wherein said internal standard is rabbit phosphorylase B.

10. A method according to claim 8, wherein said internal standard is bovine carbonic anhydrase.

11. A method according to claim 1, wherein the protease inhibitor comprises at least one substance selected from the group consisting of MINI COMPLETE and PEFABLOC.

12. A method according to claim 11, wherein the solvent used in step (a) to dissolve the sample is Lp3 composed of 1.5 mg MINI COMPLETE dissolved in 2 ml lysis buffer of 7M urea, 2M thiourea, 4% (w/v) CHAPS, 1% (w/v) DTT, and 0.5% PHARMALYTE pH 3-10; and: 1 mg PEFABLOC dissolved in 2 ml lysis buffer; in a ratio 1:1 w/v.

13. A method according to claim 1, wherein said enzyme mixture comprises a protein or peptide fraction having a molecular weight above about 8 kD.

14. A method according to claim 1, wherein the identity of a pancreatin sample is identified.

15. A method according to claim 1, wherein the protein or peptide pattern of a pancreatin sample is identified.

16. A method according to claim 1, wherein the identity, protein pattern and peptide pattern of a pancreatin sample are identified.

17. A method according to claim 16, further comprising identifying protein or peptide spots using MALDI-TOF-MS.

18. A method according to claim 1, wherein said method is a stress or stability test for determining the identity or the protein or peptide pattern of a pancreatin sample, and the presence of impurities and/or degradants.

19. A method according to claim 18, further comprising quantifying proteins, peptides, impurities and degradants present in the sample.

20. A method according to claim 13, further comprising characterizing and quantifying protein or peptide fractions with a molecular weight below about 8 kD by RP-HPLC.

21. A method of comparing a first protein sample to a second protein sample by two-dimensional gel electrophoresis, wherein each protein sample contains a physiologically acceptable digestive enzyme mixture with lipolytic, proteolytic and amylolytic activity and wherein one of the mixtures can be used in the manufacture of a pharmaceutical preparation, said method comprising:
 (a) preparing the first protein sample and second protein sample by separately dissolving each sample in a gel electrophoresis solvent composition comprising a protein solving solvent, an internal standard for quantifying proteins, and a protease inhibitor;
 (b) defining the first dimension of the gel electrophoresis by isoelectric focusing, and applying a gradient to separate the protein fractions in the first sample and the second sample;
 (c) re-buffering the protein fractions of the first sample and the second sample;
 (d) transferring the protein fractions of the first sample from (c) to the second dimension of the gel electrophoresis and separating components of the fractions by SDS-PAGE;
 (e) transferring the protein fractions of the second sample from (c) to the second dimension of the gel electrophoresis and separating components of the fractions by SDS-PAGE;
 (f) fixing and staining a first SDS-PAGE gel resulting from (d) and a second SDS-PAGE gel resulting from (e); and
 (g) comparing the first gel resulting from (f) to the second gel resulting from (f).

22. A method according to claim 1, wherein the internal standard is a combination of phosphorylase B and carbonic anhydrase.

\* \* \* \* \*